(12) United States Patent
Nishihara et al.

(10) Patent No.: US 10,912,929 B2
(45) Date of Patent: Feb. 9, 2021

(54) TUBULAR BODY

(71) Applicant: ASAHI INTECC CO., LTD., Aichi (JP)

(72) Inventors: Hiroyuki Nishihara, Osaka (JP); Aya Takechi, Osaka (JP)

(73) Assignee: ASAHI INTECC CO., LTD., Seto (JP)

( * ) Notice: Subject to any disclaimer, the term of this patent is extended or adjusted under 35 U.S.C. 154(b) by 37 days.

(21) Appl. No.: 16/374,747

(22) Filed: Apr. 3, 2019

(65) Prior Publication Data

US 2020/0069918 A1 Mar. 5, 2020

(30) Foreign Application Priority Data

Sep. 5, 2018 (JP) ................................ 2018-165635

(51) Int. Cl.
*F16L 11/00* (2006.01)
*A61M 25/09* (2006.01)
(Continued)

(52) U.S. Cl.
CPC ............... *A61M 25/09* (2013.01); *D07B 1/12* (2013.01); *A61M 2025/09066* (2013.01);
(Continued)

(58) Field of Classification Search
CPC ........ A61M 25/09; A61M 2025/09066; A61M 2025/09133; D07B 1/12;
(Continued)

(56) References Cited

U.S. PATENT DOCUMENTS 338,913 A * 3/1886 Batchelor .............. D07B 5/007
57/215
424,044 A * 3/1890 Almond .................. F16L 11/16
138/134
(Continued)

FOREIGN PATENT DOCUMENTS

EP 2 586 483 A1 5/2013
JP 57-59519 A 4/1982
(Continued)

OTHER PUBLICATIONS

Extended European Search Report dated Jan. 28, 2020 in European Patent Application No. 19188785.0, 7 pages.

*Primary Examiner* — James F Hook
(74) *Attorney, Agent, or Firm* — Xsensus LLP

(57) ABSTRACT

A tubular body that includes a plurality of first wires distributed in an annular portion of the tubular body, and a plurality of deformed second wires alternately disposed between each of the plurality of first wires, the plurality of first wires and the plurality of deformed second wires being in an alternately twisted arrangement in a longitudinal direction of the tubular body, where each of the plurality of first wires has a substantially circular shape in a cross section view, and each of the plurality of deformed second wires has a non-circular shape in the cross section view, has an arcuate side portion that receive a part of a side surface of an adjacent wire of the plurality of first wires, and has an annular sector shape protruding in a radial direction in the cross section view of the tubular body.

16 Claims, 15 Drawing Sheets

(51) Int. Cl.
*D07B 1/12* (2006.01)
*F16L 11/16* (2006.01)

(52) U.S. Cl.
CPC ............. *A61M 2025/09133* (2013.01); *A61M 2025/09191* (2013.01); *D07B 2201/2002* (2013.01); *D07B 2201/2009* (2013.01); *D07B 2205/3021* (2013.01); *F16L 11/16* (2013.01)

(58) Field of Classification Search
CPC .... D07B 2201/2009; D07B 2201/2002; D07B 2205/3021; F16L 11/16
USPC .......................................... 138/117, 129, 134
See application file for complete search history.

(56) References Cited

U.S. PATENT DOCUMENTS

| | | | | | |
|---|---|---|---|---|---|
| 969,660 | A | * | 9/1910 | Schmidt | F16D 3/72 464/58 |
| 1,164,521 | A | * | 12/1915 | Houben | F16L 11/16 138/134 |
| 2,087,876 | A | * | 7/1937 | Peterson | H01B 5/101 138/134 |
| 2,117,818 | A | * | 5/1938 | Oechslin | D07B 1/08 57/215 |
| 3,445,586 | A | * | 5/1969 | Edwards | H01B 5/00 174/130 |
| 3,858,616 | A | * | 1/1975 | Thiery | E21B 17/20 138/133 |
| 5,169,729 | A | * | 12/1992 | Maiocchi | B60C 15/04 428/589 |
| 6,137,060 | A | * | 10/2000 | Avellanet | A61M 25/09 174/128.1 |
| 8,286,949 | B2 | * | 10/2012 | Amils | E01F 15/06 256/46 |
| 2002/0072689 | A1 | * | 6/2002 | Klint | A61M 25/09025 600/585 |
| 2002/0151823 | A1 | * | 10/2002 | Miyata | A61M 25/09 600/585 |
| 2005/0154400 | A1 | | 7/2005 | Kato et al. | |
| 2010/0147435 | A1 | * | 6/2010 | Yamazaki | D07B 1/062 152/540 |
| 2017/0156745 | A1 | | 6/2017 | Okada | |
| 2018/0071495 | A1 | | 3/2018 | Yonezawa | |

FOREIGN PATENT DOCUMENTS

| | | |
|---|---|---|
| JP | 2005-230132 A | 9/2005 |
| JP | 2010-136895 A | 6/2010 |
| JP | 4810388 B2 | 11/2011 |

\* cited by examiner

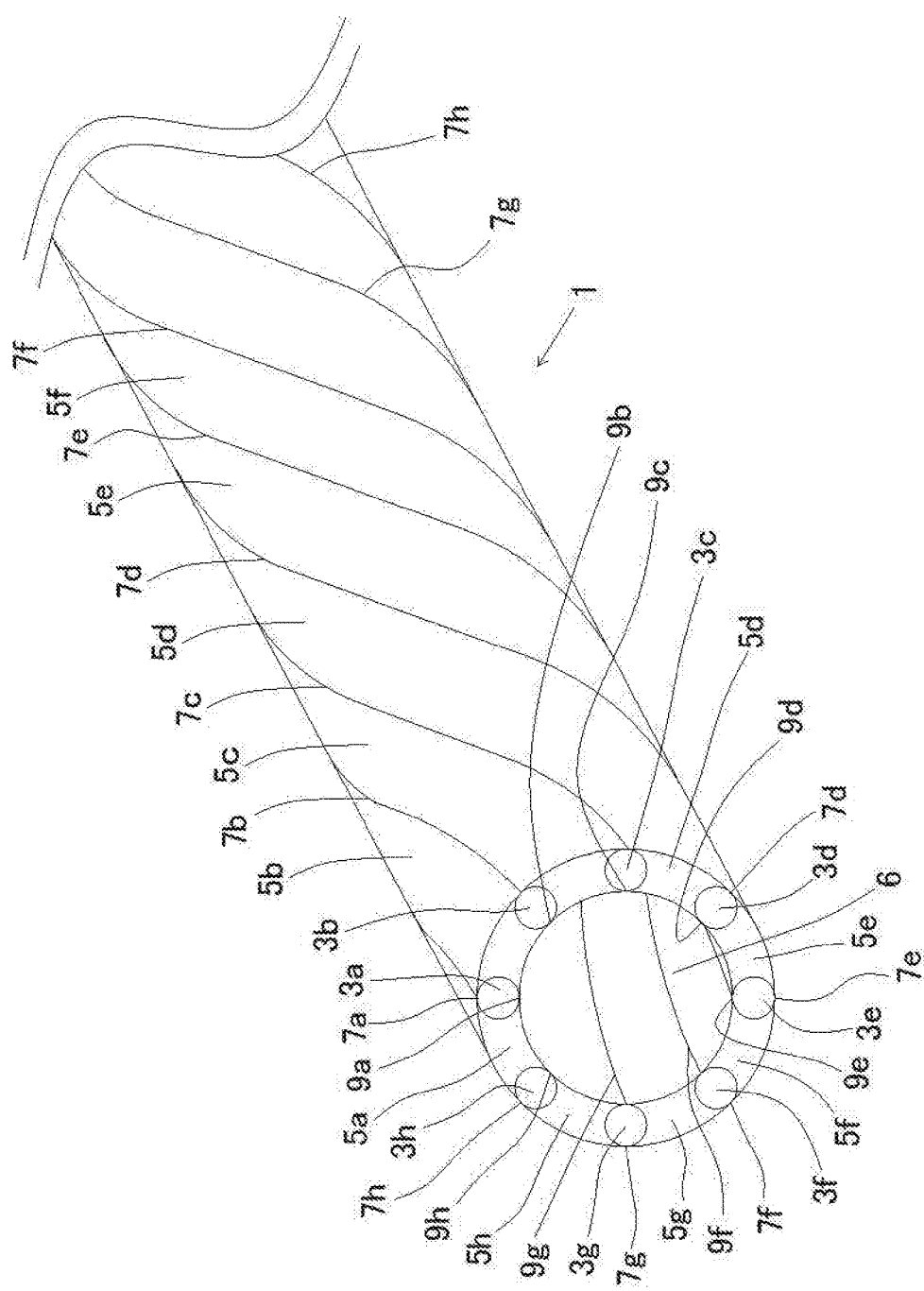
[FIG.01]

[FIG.02]
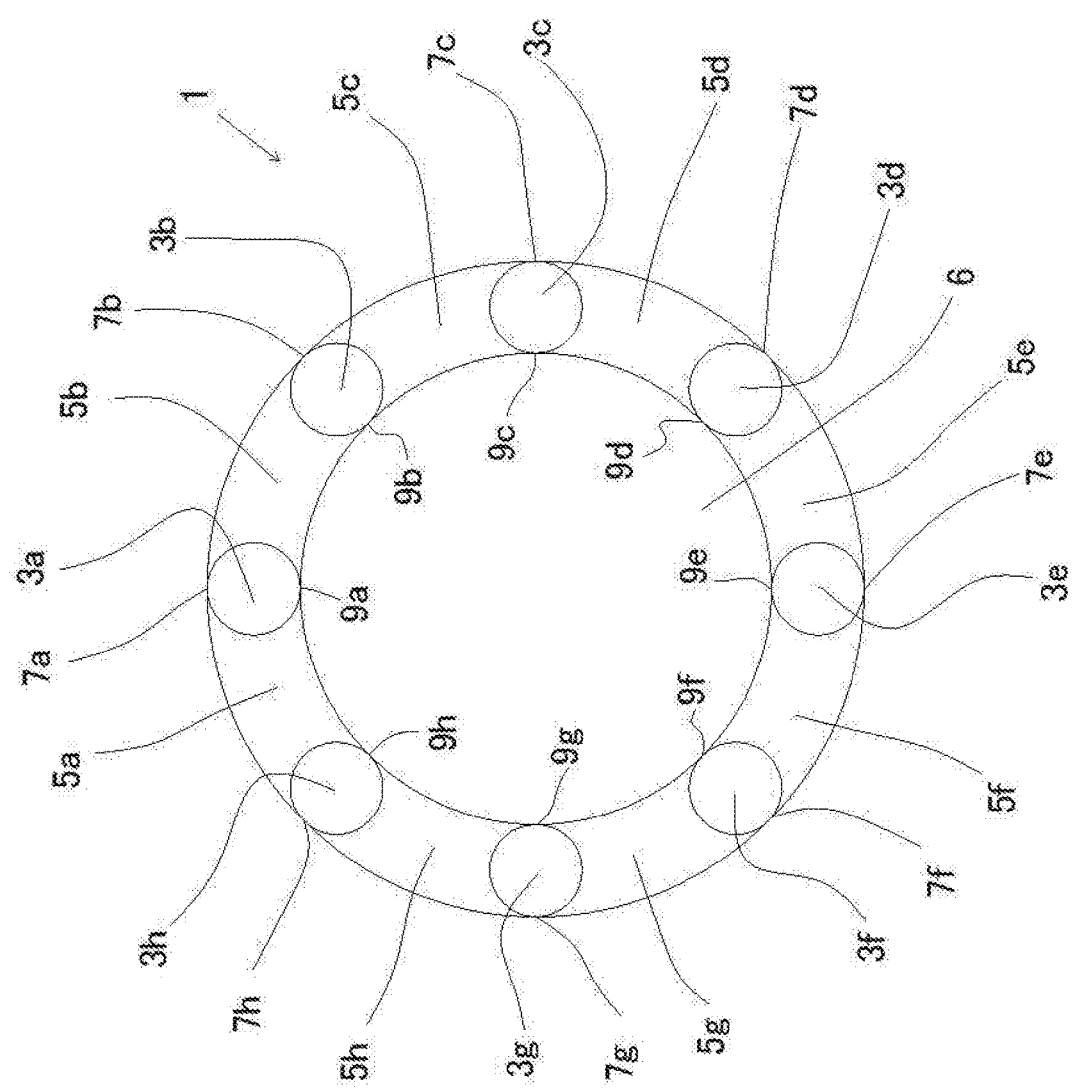

[FIG.03]
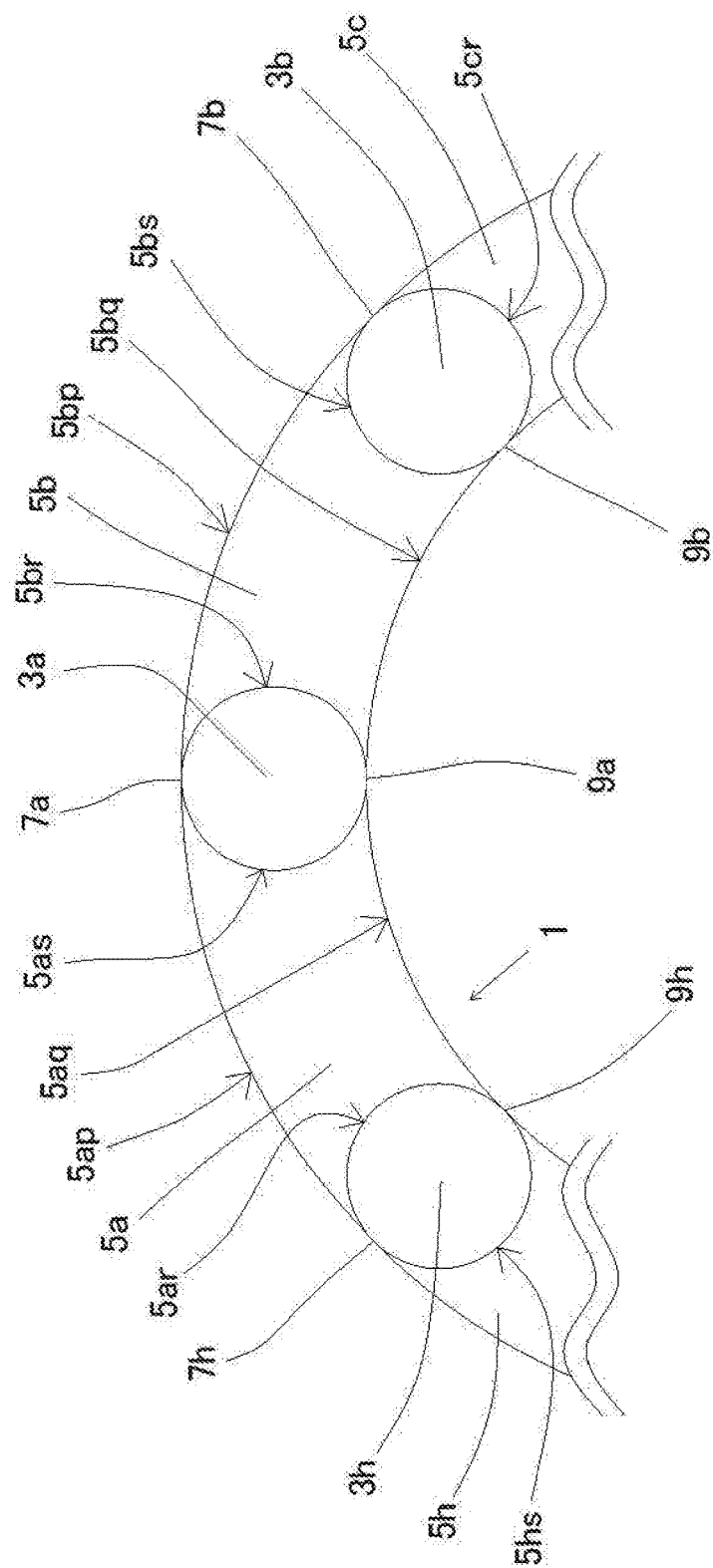

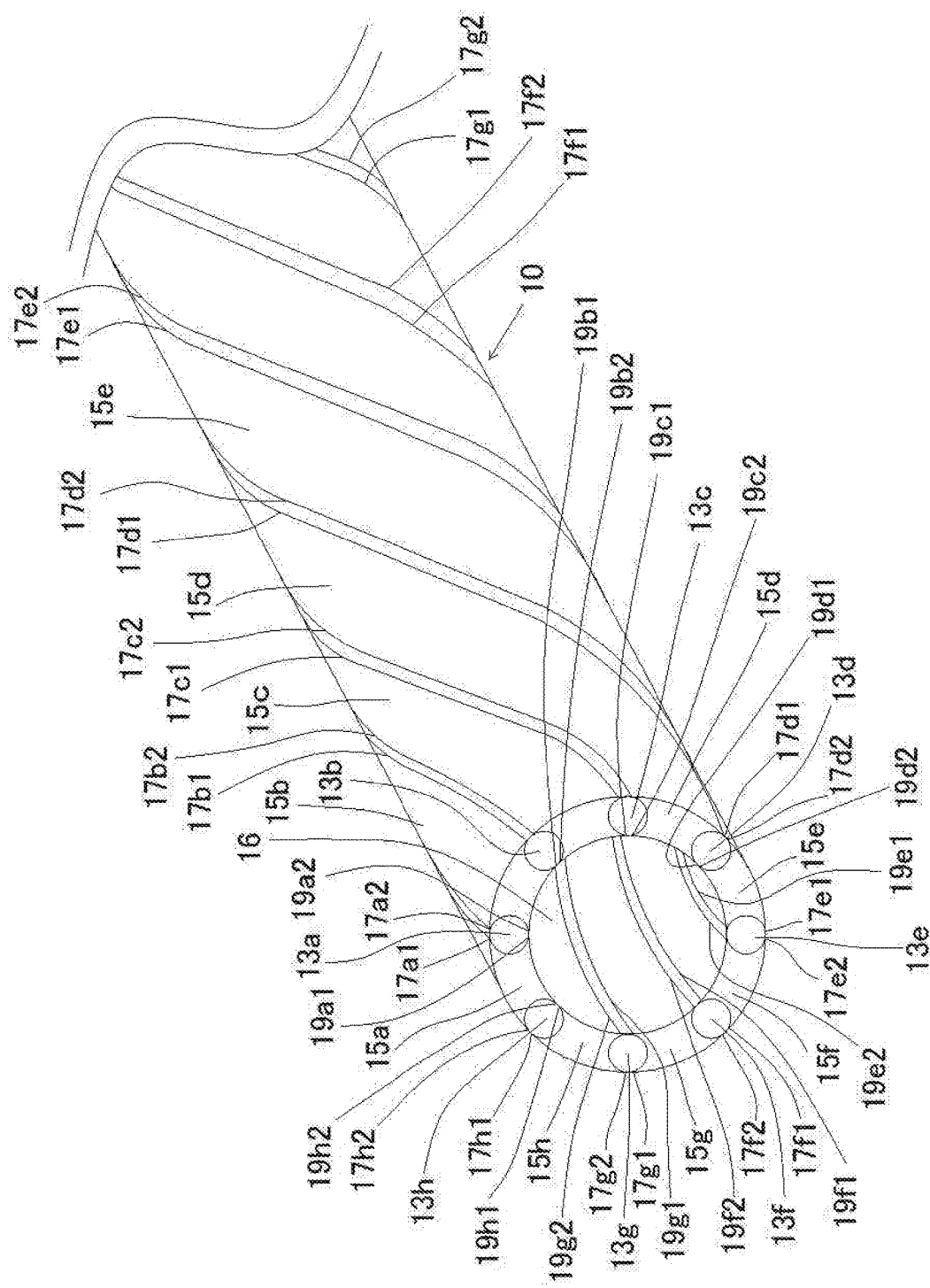
[FIG.04]

[FIG.05]
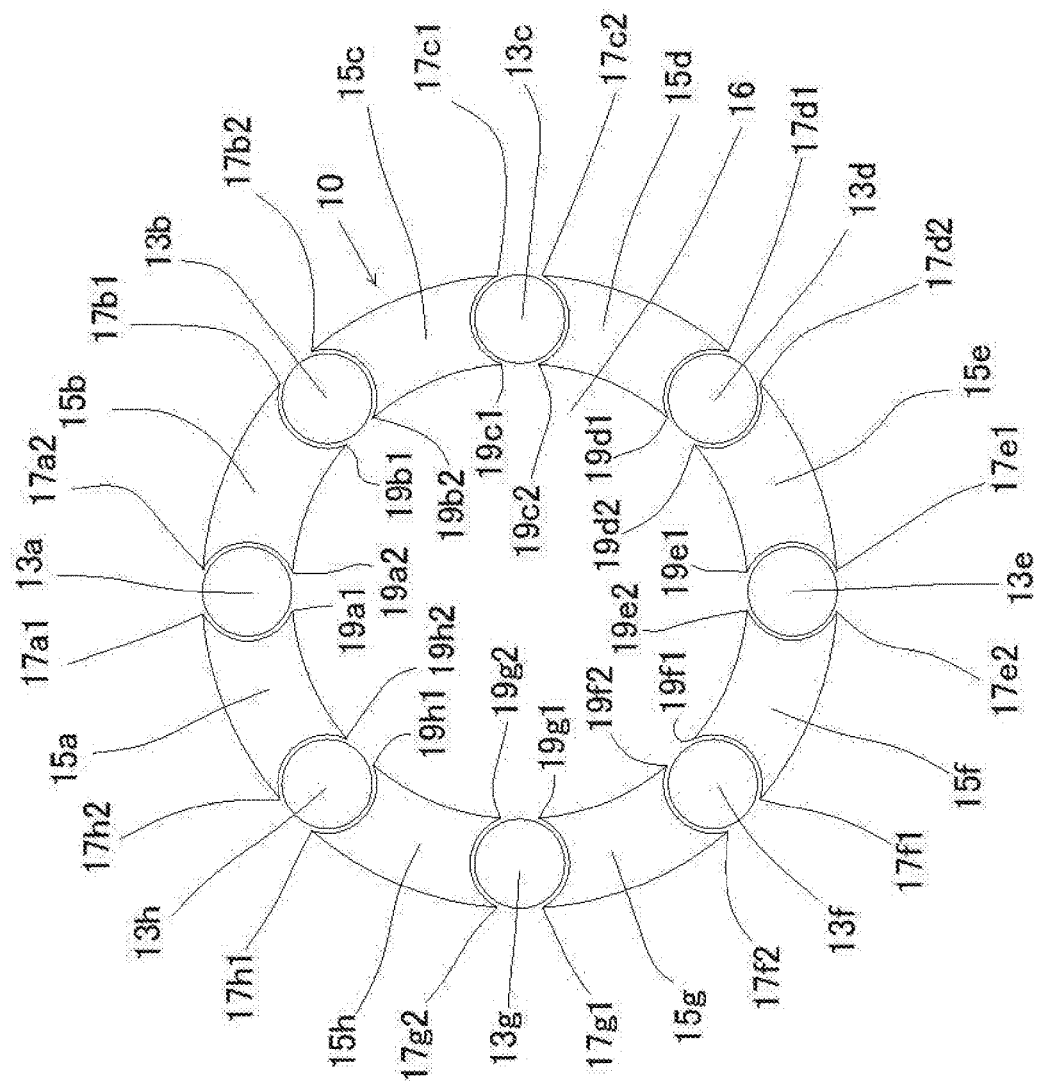

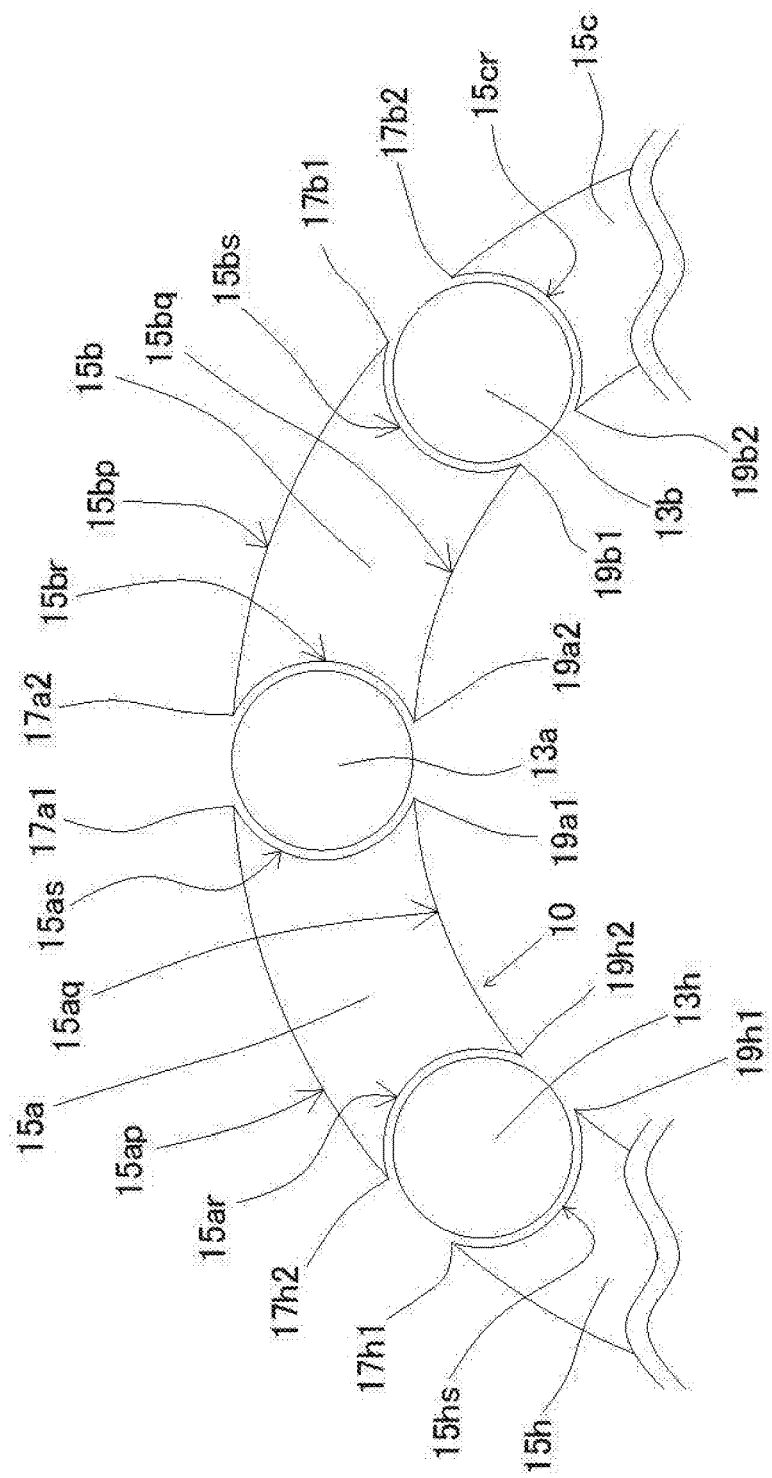
[FIG.06]

[FIG.07]
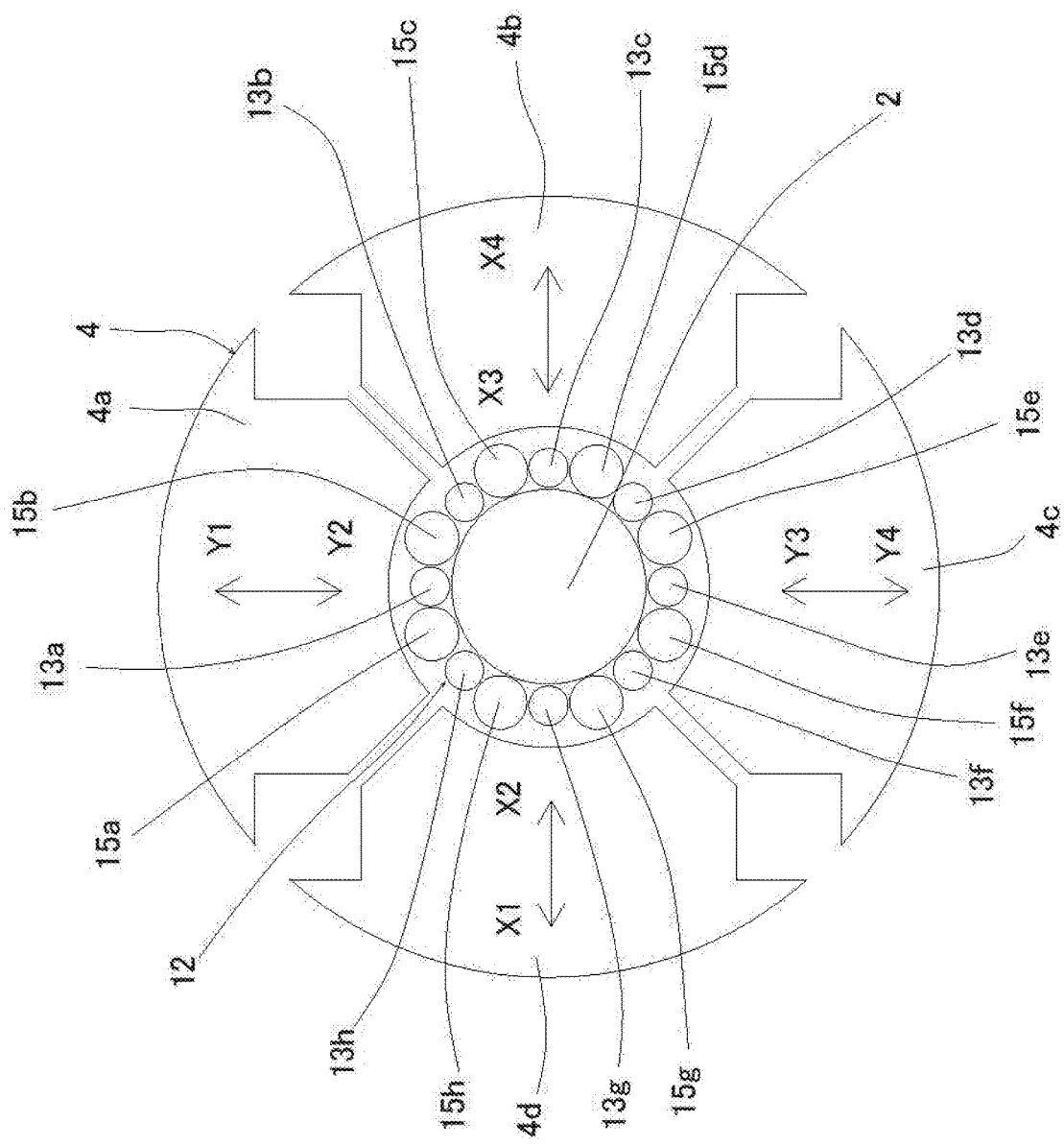

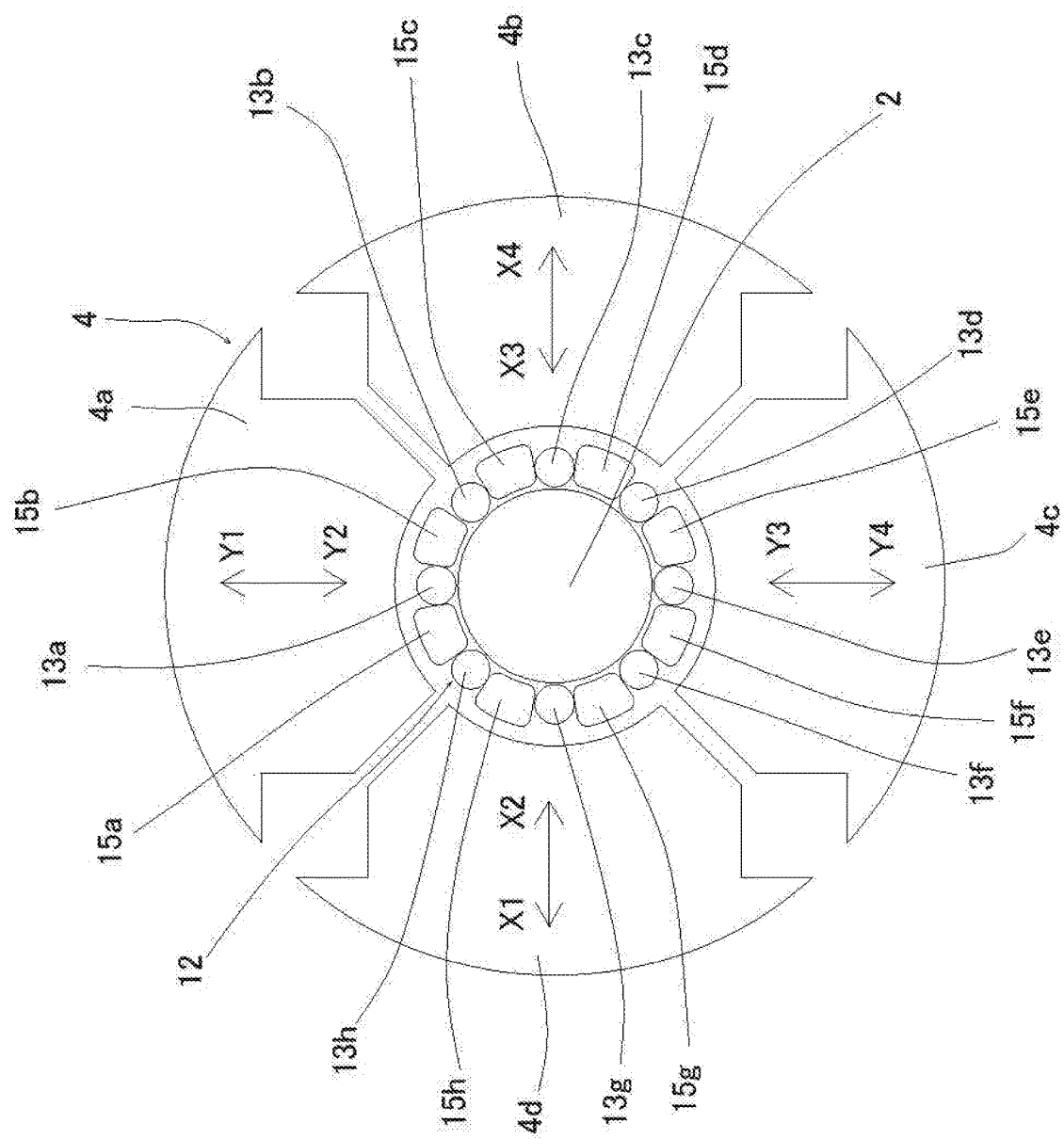
[FIG.08]

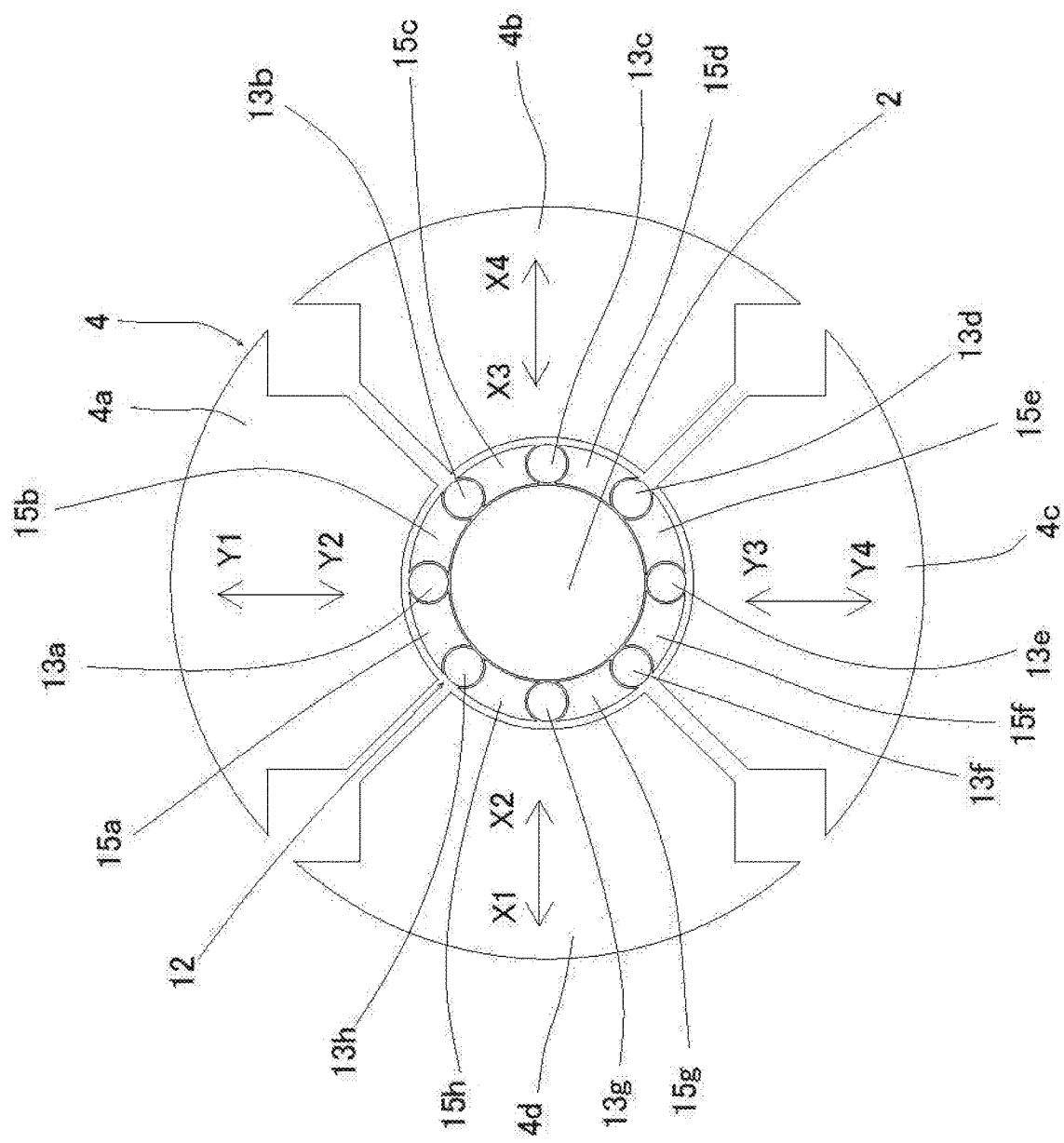
[FIG.09]

[FIG.10]
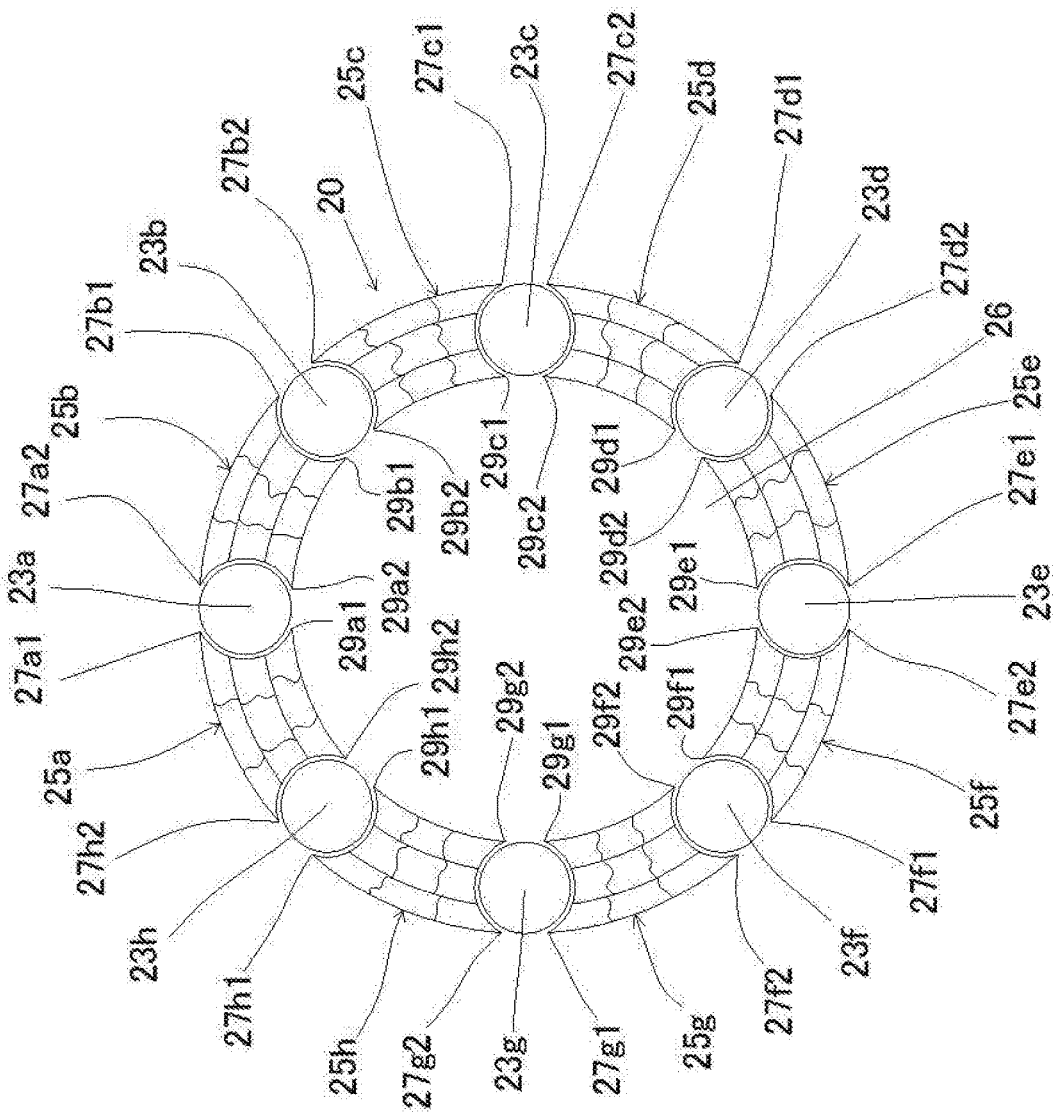

[FIG.11]
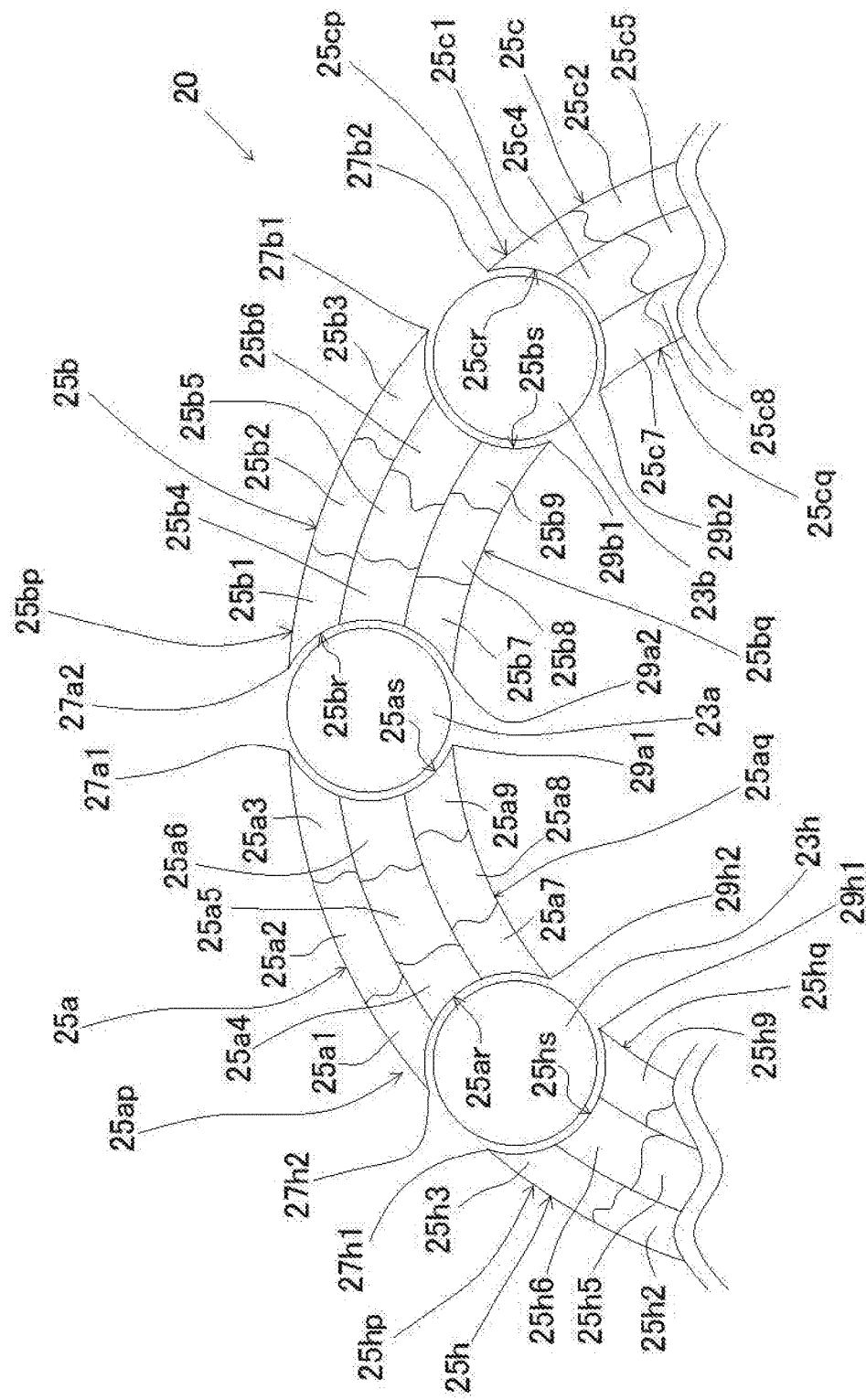

[FIG.12]
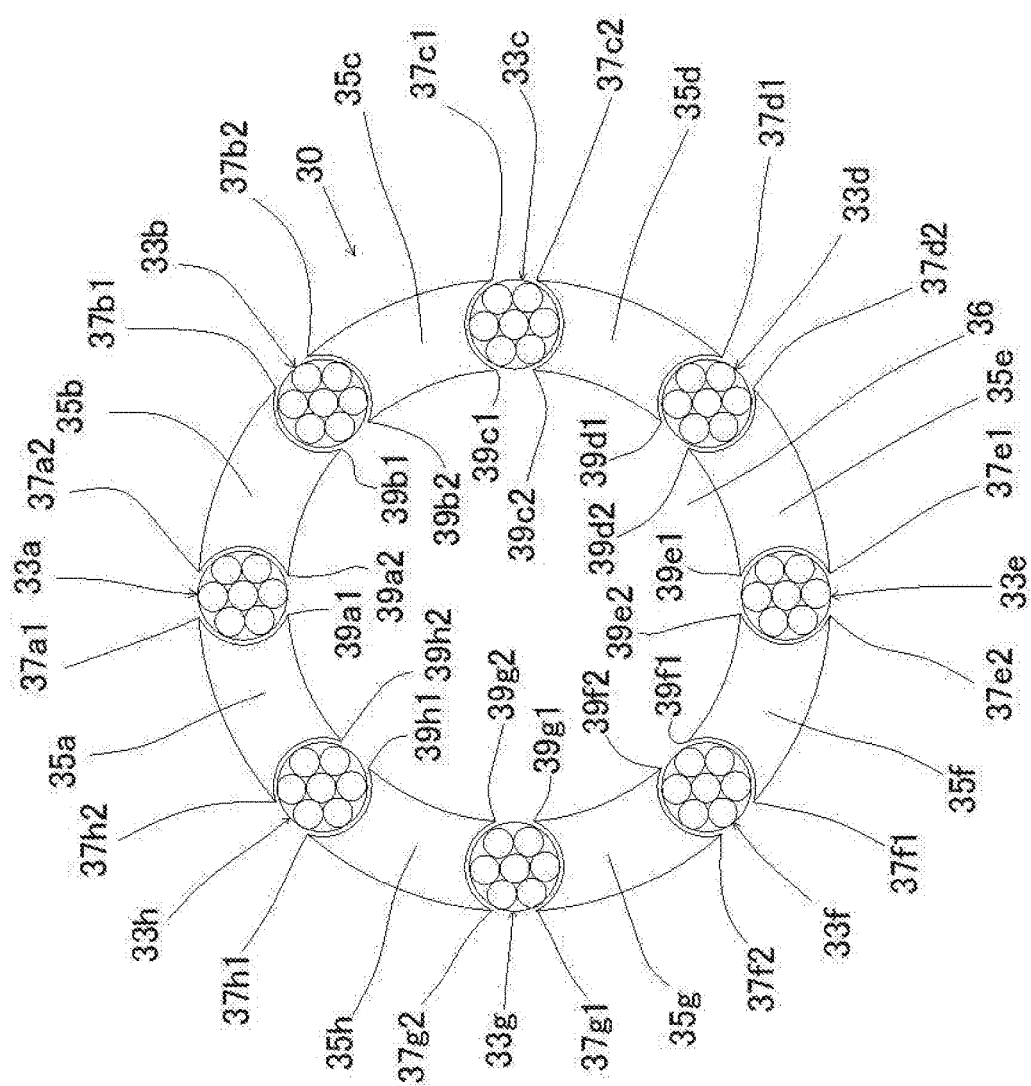

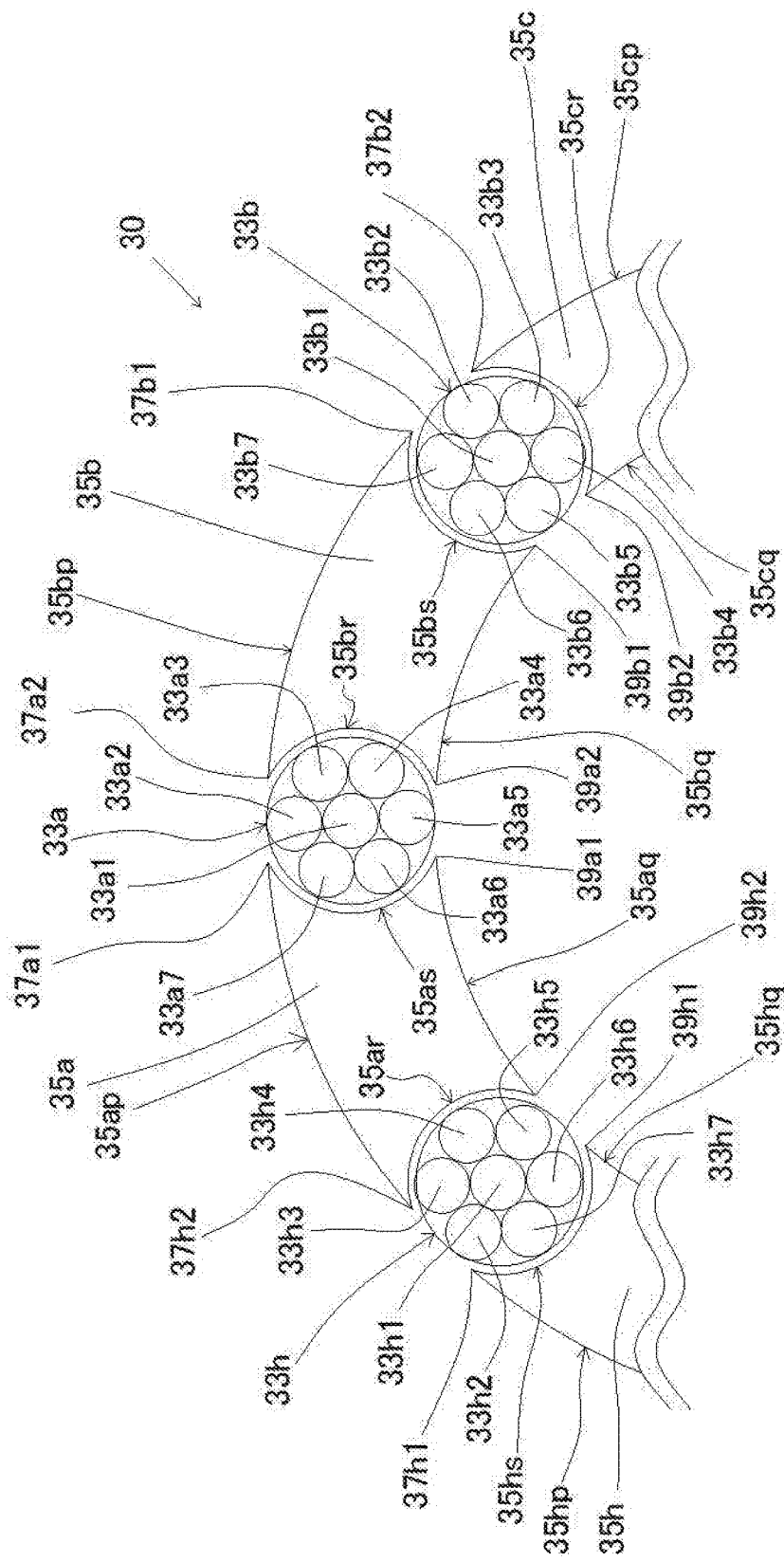
[FIG.13]

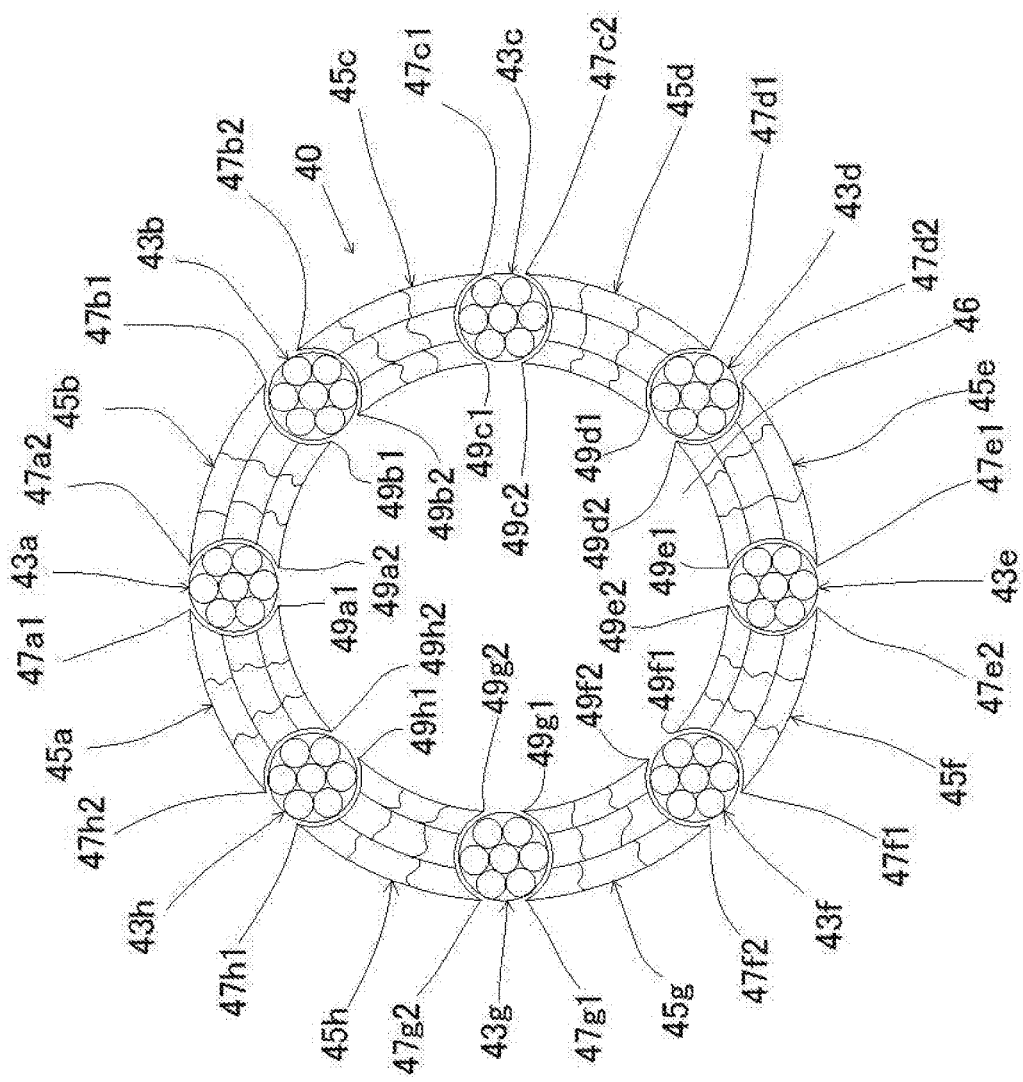

[FIG.15]
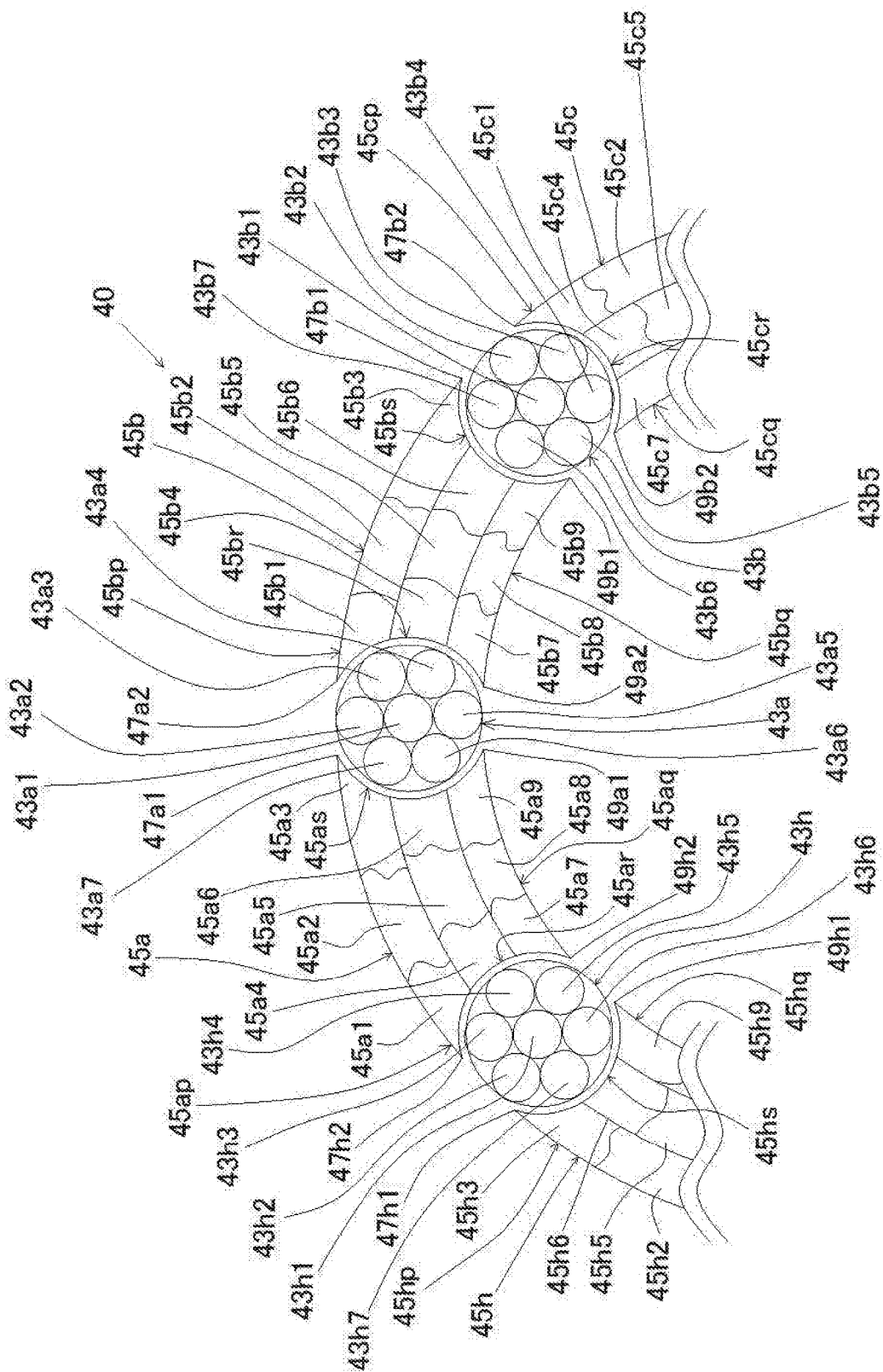

TUBULAR BODY

CROSS REFERENCE TO RELATED APPLICATION

This application claims priority to Japanese Patent Application 2018-165635, filed on Sep. 5, 2018, which is incorporated herein by reference.

TECHNICAL FIELD

The present disclosure relates to a tubular body that is configured by twisting a plurality of wires.

BACKGROUND

Conventionally, in a catheter percutaneously inserted into a blood vessel, from the viewpoint of the performance of pushability for transmitting pushing force of an operator to a distal end portion of the catheter, torque transmissibility for transmitting a rotative force to the distal end portion of the catheter when the operator rotates a proximal end portion of the catheter, kink resistance not causing bent at the bent portion or the curved portion of the blood vessel, and insertability of another medical devices into the catheter lumen and so on, various medical tube suitable for catheters have been developed.

For example, Patent Document 1 discloses a medical tube including a coil layer which a flat wire (its cross section is rectangular) is densely wound is arranged on an inner layer of the medical tube, and an outer layer of polyamide elastomer is arranged on an outside of the coil layer (see FIG. 1 etc.). Patent Document 1 also discloses that it is possible to achieve all of flexibility, good kink resistance, and good tensile strength according to this medical tube (see paragraph [0006] etc.).

PRIOR ART DOCUMENTS

Patent Document

[Patent Document 1] JP 2010-136895 A

SUMMARY

The present application provides a tubular body, comprising: a plurality of first wires distributed in an annular portion of the tubular body; and a plurality of deformed second wires alternately disposed between each of the plurality of first wires, the plurality of first wires and the plurality of deformed second wires being in an alternately twisted arrangement in a longitudinal direction of the tubular body, wherein each of the plurality of first wires has a substantially circular shape in a cross section view with respect to the longitudinal direction of the tubular body, and each of the plurality of deformed second wires has a non-circular shape in the cross section view, has an arcuate side portion that receive a part of a side surface of an adjacent wire of the plurality of first wires, and has an annular sector shape protruding in a radial direction in the cross section view of the tubular body.

BRIEF DESCRIPTION OF THE DRAWINGS

FIG. 1 is a perspective view of the tubular body of the first embodiment of the present disclosure.

FIG. 2 is a cross-sectional view of the tubular body of the first embodiment.

FIG. 3 is a partially enlarged view of FIG. 2.

FIG. 4 is a perspective view of the tubular body of the second embodiment.

FIG. 5 is a cross-sectional view of the tubular body of the second embodiment.

FIG. 6 is a partially enlarged view of FIG. 5.

FIG. 7 is a cross-sectional view showing an initial state of setting a stranded wire to a swaging machine in producing a tubular body of the second embodiment.

FIG. 8 is a cross-sectional view showing an intermediate state in producing the tubular body of the second embodiment.

FIG. 9 is a cross-sectional view showing a final state in producing the tubular body of the second embodiment.

FIG. 10 is a cross-sectional view of the tubular body of the third embodiment.

FIG. 11 is a partially enlarged view of FIG. 10.

FIG. 12 is a cross-sectional view of the tubular body of the fourth embodiment.

FIG. 13 is a partially enlarged view of FIG. 12.

FIG. 14 is a cross-sectional view of the tubular body of the fifth embodiment.

FIG. 15 is a partially enlarged view of FIG. 14.

DETAILED DESCRIPTION

Problems that the Disclosure is to Solve

However, the coils used in the medical tube disclosed in Patent Document 1, since the wire is wound is flat wire (its cross section is rectangular), when one end portion of the medical tube is operated, there was a problem that the wire itself deviates in cross section radially inside or outside of the coil from adjacent wires.

Therefore, in the medical tube disclosed in Patent Document 1, in order to prevent the deviation of the wire, the outer tube made of polyamide elastomer is coated on the outside of the coil (see paragraph [0042] etc.).

Incidentally, when the user manipulates one end portion of the medical tube, a problem that the wire itself deviates in cross section radially inside or outside of the coil against the wires adjacent to both sides, has occurred even if the wire forming the coil is a round wire (circular cross section) not only in the case of a flat wire (rectangular cross section).

Incidentally, when the wire constituting the coil is a round wire (circular cross section) compared with the case of the wire constituting the coil is a flat wire, because the inner surface of the coil is more uneven, a problem that the insertion resistance of the medical device into an inside of the coil is even worse has occurred.

The present disclosure has been made in response to the above problems the aforementioned prior art has. When the user manipulates one end portion portion of the coil (hereinafter, referred to as "tubular body"), the present disclosure may prevents the misalignment between the wires, may improve the torque transmissibility and pushing force to the other end portion of the tubular body, and may improve the insertability of the medical device into the inside of the tubular body, and further may improve flexibility and improve durability.

Means for Solving the Problems

To solve the problems described above, the first aspect of the present disclosure comprises a plurality of first wires, a plurality of second wires twisted with the plurality of first wires, wherein at least one of the first wires has a substantially circular cross section, each of at least one of the second wires corresponding to the at least one of the first wires has a recess in the contact portion between adjacent the first wires, and a convex shape cross section in the transverse plane radial direction.

The second aspect of the present disclosure is a tubular body of the first aspect, wherein each of the plurality of second wires is configured by twisting a plurality of third wires.

The third aspect of the present disclosure is a tubular body of the first or second aspect, wherein each of the plurality of first wires is configured by twisting a plurality of fourth wires.

Furthermore, a fourth aspect of the present disclosure, in any one of the tubular body according to claim 1 to claim 3, wherein each of the plurality of the second wires is formed by deforming the wire of larger outer diameter than an outer diameter of the first wire.

Effect of the Disclosure

As a first aspect of the present disclosure comprises a plurality of first wires, a plurality of second wires twisted with the plurality of first wires, wherein at least one of the first wires has a substantially circular cross section, each of at least one of the second wires corresponding to the at least one of the first wires has a recess in the contact portion between adjacent the first wires, and a convex shape cross section in the transverse plane radial direction, when the user manipulates one end portion portion of the tubular body, it is possible to prevent the deviation between the first wire and the second wire, to improve the torque transmissibility and pushing force to the other end portion of the tubular body. Further, it is possible to improve insertability of a medical device into the inside of the tubular body.

According to the second aspect of the present disclosure, in the tubular body of the first aspect, as each of the plurality of second wires is configured by twisting a plurality of third wires, in addition to the effect of the first aspect of the disclosure, when the tubular body is curved, by the subtle movement of the third wire, the flexibility and durability may be improved.

According to the third aspect of the present disclosure, in a tubular body of the first or second aspect, as each of the plurality of first wires is configured by twisting a plurality of fourth wires, in addition to the effect of the tubular body of the first or second aspect, when the tubular body is curved, by the subtle movement of the fourth wire, the flexibility and durability may also be further improved.

Further, according to the fourth aspect of the present disclosure, in any one of the tubular body of the first aspect to the third aspect, as each of the plurality of the second wires is formed by deforming the wire of larger outer diameter than an outer diameter of the first wire, in addition to the effect of any of the tubular body of the first aspect to the third aspect, the second wire is sufficiently filled between the first wires, when the user manipulates one end portion of the tubular body, it is possible to prevent the deviation between the first wire and the second wire, to improve the torque transmission and pushing force to the other end portion of the tubular body.

EMBODIMENT OF THE PRESENT DISCLOSURE

Hereinafter, embodiments of the present disclosure will be described with reference to the drawings.

First Embodiment

Firstly, a first embodiment of the present disclosure will be described. FIG. 1 is a perspective view of the tubular body of the first embodiment of the present disclosure, FIG. 2 is a cross-sectional view of the tubular body of the first embodiment, FIG. 3 is a partially enlarged view of FIG. 2.

As shown in FIG. 1, a tubular body 1 is elongated tubular body configured to wind eight first wires (3a, 3b, 3c, 3d, 3e, 3f, 3g, 3h) and eight second wires (5a, 5b, 5c, 5d, 5e, 5f, 5g, 5h) alternately hollow spirally.

Further, the tubular body 1 includes a substantially circular outer peripheral surface and a substantially circular inner peripheral surface in a cross-sectional view, and the tubular body 1 forms a hollow portion 6 in an inside of the inner peripheral surface thereof.

The first wire of the present embodiment (3a~3h) is substantially circular in a cross-sectional view. Here, the reason why the first wires (3a~3h) are described as substantially circular not exactly circular in a cross-sectional view depends on considering a case where the first wire is slightly deformed by the manufacturing method of the tubular body described below. However, the first wires (3a~3h) are substantively good to be circular in a cross-sectional view.

On the other hand, each of the second wires (5a~5h) of the present embodiment has a recess in the contact portion between the first wires adjacent to both sides. For example, the second wire 5a has a recess 5ar in the contact portion between the second wire 5a and the first wire 3h, and a recess 5as in the contact portion between the second wire 5a and the first wire 3a as shown in FIG. 3.

The second wire 5b has a recess 5br in the contact portion between the second wire 5b and the first wire 3a, and a recess 5bs in the contact portion between the second wire 5b and the first wire 3b. Further, other second wires (5c, 5d, 5e, 5f, 5g, 5h) also have recesses 5cr, recess 5cs (not shown), . . . , recess 5hr (not shown), recess 5hs. It will be easily understood.

The second wire (5a~5h) of the present embodiment has a convex annular sector shape (arch shape) in the transverse plane radial direction. For example, the second wire 5a has an annular sector shape (arch shape) having a convex outer arc 5ap and a convex inner arc 5aq in the transverse plane radial direction as shown in FIG. 3.

The second wire 5b has an annular sector shape (arch shape) having a convex outer arc 5bp and a convex inner arc 5bq in the transverse plane radial direction. Further, other second wires (5c, 5d, 5e, 5f, 5g, 5h) also have annular sector shape (arch shape) having a convex outer arc and a convex inner arc in the transverse plane radial direction. It will be easily understood.

Incidentally, in the tubular body 1 of the present embodiment, each end of two second wires adjacent to both sides of the first wire is in contact with each one point of the outside and inside. For example, in two second wires 5a and 5b adjacent to both sides of the first wire 3a, two ends of the outer side are in contact with one point 7a, the two ends of the inner side are also in contact with one point 9a as shown in FIGS. 1 to 3.

Thus, a helical pattern through point 7a is formed on the outer surface of the tubular body 1, and a helical pattern through point 9a is formed on the inner surface of the tubular body 1.

Similarly, as the ends of two second wires adjacent to each both sides of other first wires (3b, 3c, 3d, 3e, 3f, 3g, 3h) are also contact with one point of the outer side and the inner side, seven helical patterns by point 7b, 7c, 7d, 7e, 7f, 7g and 7h are formed on the outer surface of the tubular body 1, and seven helical patterns by point 9b, 9c, 9d, 9e, 9f, 9g and 9h are formed on the inner surface of the tubular body 1.

Materials of the first wires (3a~3h) and a second wire (5a~5h) are stainless steel, platinum alloys, Ni—Ti-based alloys, cobalt based alloys such as, it is not particularly limited to them. Any material having a biocompatible is available, and stainless steel is used in the present embodiment.

The first wires (3a~3h) and a second wires (5a~5h) are formed of the same material as in the present embodiment, they may be formed of a different material. However, when a tubular body 1 is produced by the method according to a swaging machine to be described later, It is preferred that the material of the second wires (5a~5h) are softer than the material of the first wires (3a~3h).

According to the tubular body 1 of the present embodiment, as the tubular body 1 is configured to wind eight first wires (3a~3h) and eight second wires (5a~5h) alternately in a hollow shape, each of first wires (3a~3h) is a substantially circular cross section, each of second wires (5a~5h) has a recess (5ar, 5as, 5br, 5bs, 5cr . . . 5hs) in contact portion between the first wire adjacent to it, has an annular sector shape (arch shape) having a convex outer arc (5ap, 5bp, . . . , 5hp (not shown)) and a convex inner arc (5aq, 5bq, . . . 5hq (not shown)) in the transverse plane radial direction, when the user manipulates one end portion of the tubular body 1, it is possible to prevent the deviation between the first wires and the second wires, improve the torque transmissibility and pushing force to the other end portion of the tubular body 1. Further, since the inner surface of the tubular body 1 is flat in a vertical cross-sectional view, it may improves insertability of other medical devices into an inside of the tubular body 1.

In the present embodiment, the number of the first wire and the second wire is eight each, it is not limited to eight. Two or more first wires and two or more second wires may be used in a tubular body. That is, it may be a tubular body comprising a plurality of first wires and a plurality of second wires.

Second Embodiment

Next, a second embodiment of the present disclosure will be described.

FIG. 4 is a perspective view of the tubular body of the second embodiment, FIG. 5 is a cross-sectional view of the tubular body of the second embodiment, FIG. 6 is a partially enlarged view of FIG. 5.

As shown in FIG. 4, a tubular body 10 is elongated tubular body configured to wind eight first wires (13a, 13b, 13c, 13d, 13e, 13f, 13g, 13h) and eight second wires (15a, 15b, 15c, 15d, 15e, 15f, 15g, 15h) alternately hollow spirally.

Further, the tubular body 10 includes a substantially circular outer peripheral surface and a substantially circular inner peripheral surface in a cross-sectional view, and the tubular body 10 forms a hollow portion 16 in an inside of the inner peripheral surface thereof.

Each of the first wires (13a~13h) of the present embodiment is substantially circular in a cross-sectional view. Here, the reason why the first wires (13a~13h) are described as substantially circular not exactly circular in a cross-sectional view depends on considering a case where the first wire is slightly deformed by the manufacturing method of the tubular body described below. However, the first wires (13a~13h) are substantively good to be circular in a cross-sectional view.

On the other hand, each of the second wires (15a~15h) of the present embodiment has a recess in the contact portion between the first wires adjacent to both sides. For example, the second wire 15a has a recess 15ar in the contact portion between the second wire 15a and the first wire 13h, and a recess 15as in the contact portion between the second wire 15a and the first wire 13a as shown in FIG. 6.

The second wire 15b has a recess 15br in the contact portion between the second wire 15b and the first wire 13a, and a recess 15bs in the contact portion between the second wire 15b and the first wire 13b. Further, other second wires (15c, 15d, 15e, 15f, 15g, 15h) also have recesses 15cr, recess 15cs (not shown), . . . , recess 15hr (not shown), recess 15hs. It will be easily understood.

The second wire (15a~15h) of the present embodiment has the shape of convex annular sector shape (arch shape) in the transverse plane radial direction. For example, the second wire 15a has an annular sector shape (arch shape) having a convex outer arc 15ap and a convex inner arc 15aq in the transverse plane radial direction as shown in FIG. 6.

The second wire 15b has an annular sector shape (arch shape) having a convex outer arc 15bp and a convex inner arc 15bq in the transverse plane radial direction. Further, other second wires (15c, 15d, 15e, 15f, 15g, 15h) also have annular sector shape (arch shape) having a convex outer arc and a convex inner arc in the transverse plane radial direction. It will be easily understood.

Incidentally, the tubular body 10 of the present embodiment differs from the tubular body 1 of the first embodiment, each of the ends of two second wires adjacent to both sides of the first wire are separated. For example, an outer end 17a1 of the second wire 15a adjacent to one side of the first wire 13a, and an outer end 17a2 of the second wire 15b adjacent to the other side of the first wire 13a are spaced apart, further, an inner end 19a1 of the second wire 15a adjacent to one side of the first wire 13a, and an inner end 19a2 of the second wire 15b adjacent to the other side of the first wire 13a are also spaced apart as shown in FIGS. 4 to 6.

Similarly, in the other first wire 13b~13h, an outer end 17b1 and an outer end 17b2, an outer end 17c1 and an outer end 17c2, . . . , an outer end 17g1 and an outer end 17g2, an outer end 17h1 and an outer end 17h2 are spaced apart, an inner end 19b1 and an inner end 19b2, an inner end 19c1 and an inner end 19c2, . . . , an inner end 19g1 and an inner end 19g2, an inner end 19h1 and the inner end 19h2 are also spaced apart.

Accordingly, two helical patterns per one first wire are formed on the outer surface and the inner surface of the tubular body 10 as shown in FIG. 4. In the present embodiment, a total of 16 helical patterns are formed on the outer surface of the tubular body 10, and a total of 16 helical patterns are formed on the inner surface of the tubular body 10.

Similar to the first wires (3a~3h) and a second wire (5a~5h) of the first embodiment, Material of the first wires (13a~13h) and a second wire (15a~15h) are stainless steel, platinum alloys, Ni—Ti-based alloys, cobalt based alloys such as, it is not particularly limited to them. Any material having a biocompatible is available, and stainless steel is used in the present embodiment.

The first wires (13a~13h) and a second wires (15a~15h) are formed of the same material as in the present embodiment, they may be formed of a different material. However, when produced by the method according to a swaging machine to be described later a tubular body 10, It is preferred that the material of the second wires (15a~15h) are softer than the material of the first wires (13a~13h).

Here, a method for manufacturing the tubular body 10 will be described.

FIG. 7 is a cross-sectional view showing an initial state of setting a stranded wire to a swaging machine in producing a tubular body of the second embodiment, FIG. 8 is a cross-sectional view showing an intermediate state in producing the tubular body of the second embodiment, FIG. 9 is a cross-sectional view showing a final state in producing the tubular body of the second embodiment.

Incidentally, a swaging machine used to produce the tubular body 10 may use any swaging machine among two-splits die, three-splits die, four-splits die and six-slits die. In the present embodiment, a manufacturing method will be described using the swaging machine with a four-splits die.

To produce the tubular body 10, firstly, a manufacturer prepares a stranded wire 12 configured to wind eight first wires (13a~13h) of circular cross-section and eight second wires (15a~15h) of circular cross-section, wherein the diameter of the second wire is larger than the diameter of the first wire, in a spiral manner around a circumference of a core wire 2.

Then, as shown in FIG. 7, the manufacturer sets the stranded wire 12 to a swaging machine 4 and deforms the stranded wire 12 by operating the swaging machine 4. Specifically, the manufacturer deforms the stranded wire 12 by vibrating a first die 4a in a direction toward Y1 and Y2, a second die 4b in a direction toward X3 and X4, a third die 4c in direction toward Y3 and Y4, and a fourth die 4d in a direction toward X1 and X2 respectively while rotating a first die 4a, a second die 4b, a third die 4c and a fourth die 4d of swaging machine 4 around the stranded wire 12.

After the manufacturer continues to operate the swaging machine 4 for a predetermined time in this way, while cross-sectional shape of each of eight first wires (13a~13h) is remained circular, cross-sectional shape of each of eight second wires (15a~15h) is deformed into annular sector shape (arch shape) having larger diameter than the diameter of each of the first wires (13a~13h) as shown in FIG. 8.

Further after the manufacturer continues to operate the swaging machine 4 for a predetermined time in this way, while cross-sectional shape of each of eight first wires (13a~13h) is remained circular, cross-section of each of the eight second wires (15a~15h) having larger diameter than the diameter of each of the first wires (13a~13h) is deformed into convex annular sector shape (arch shape) in the transverse plane radial direction having a recess in the contact portion between the first wires adjacent to both sides as shown in FIG. 9.

Then, the tubular body 10 is completed to pull out the core wire 2 from the stranded wire 12, after removing the stranded wire 12 from the swaging machine 4.

On the other hand, without removing the stranded wire 12 from the swaging machine 4, After the manufacturer continues to operate the swaging machine 4 for a further predetermined time, stranded wire 12 that each ends of two second wires adjacent to both sides of each of the first wires (13a~13h) are in contact at each one point of the outside and inside of the stranded wire in cross-sectional view is completed. Then, the tubular body 1 as shown in FIGS. 1 to 3 is completed to pull out the core wire 2 from the stranded wire 12, after removing the stranded wire 12 from the swaging machine 4.

According to the tubular body 10 of the present embodiment, as the tubular body 10 is configured to wind eight first wires (13a~13h) and eight second wires (15a~15h) alternately in a hollow shape, each of first wires (13a~13h) is a substantially circular cross section, each of second wires (15a~15h) has recesses (15ar, 15as, 15br, 15bs, 15cr . . . 15hs) in contact portion between the first wire adjacent to it, has an annular sector shape (arch shape) having convex outer arcs (15ap, 15bp, . . . , 15hp (not shown)) and inner arcs (15aq, 15bq, . . . 15hq (not shown)) in the transverse plane radial direction, when the user manipulates one end portion of the tubular body 10, it is possible to prevent the deviation between the first wires and the second wires, improve the torque transmissibility and pushing force to the other end portion of the tubular body 10.

Further, since the inner surface of the tubular body 10 is flat in a vertical cross-sectional view, it may improve insertability of other medical devices into an inside of the tubular body 10.

Furthermore, the tubular body 10 of the present embodiment differs from the tubular body 1 of the first embodiment, that is, since the ends of the two second wires adjacent to both sides of the first wire are separated, the tubular body 10 may have a somewhat flexible structure compared to the tubular body 1 of the first embodiment.

In the present embodiment, the number of the first wire and the second wire is eight each, it is not limited to eight. Two or more first wires and two or more second wires may be used in a tubular body. That is, it may be a tubular body comprising a plurality of first wires and a plurality of second wires.

Third Embodiment

Next, a description of a third embodiment of the present disclosure will be described.

FIG. 10 is a cross-sectional view of the tubular body of the third embodiment, FIG. 11 is a partially enlarged view of FIG. 10.

As shown in FIG. 10, a tubular body 20 is elongated tubular body configured to wind eight first wires (23a, 23b, 23c, 23d, 23e, 23f, 23g, 23h) and eight second wires (25a, 25b, 25c, 25d, 25e, 25f, 25g, 25h) alternately hollow spirally.

The tubular body 20 of the present embodiment differs from the tubular body 10 of the second embodiment, each of eight second wires (25a~25h) is configured to wind nine third wires. Specifically, the second wire 25a is configured to wind nine third wires (25a1, 25a2, 25a3, 25a4, 25a5, 25a6, 25a7, 25a8, 25a9), the second wire 25b is configured to wind nine third wires (25b1, 25b2, 25b3, 25b4, 25b5, 25b6, 25b7, 25b8, 25b9) as shown in FIG. 11.

Similarly, the other second wires 25c~25h are each configured to wind nine third wires (25c1~25c9, 25d1~25d9, 25e1~25e9, 25f1~25f9, 25g1~25g9, 25h1~25h9 (not one part shown)).

Further, the tubular body 20 includes a substantially circular outer peripheral surface and a substantially circular inner peripheral surface in a cross-sectional view, and the tubular body 20 forms a hollow portion 26 in an inside of the inner peripheral surface thereof.

Each of the first wires (23a~23h) of the present embodiment is substantially circular in a cross-sectional view. Here, the reason why the first wires (23a~23h) are described as substantially circular not exactly circular in a cross-sectional view depends on considering a case where the first wire is slightly deformed by the manufacturing method of the tubular body described above. However, the first wires (23a~23h) are substantively good to be circular in a cross-sectional view.

On the other hand, each of the second wires (25a~25h) of the present embodiment has a recess in the contact portion between the first wires adjacent to both sides. For example, the second wire 25a has a recess 25ar in the contact portion between the second wire 25a and the first wire 23h, and a recess 25as in the contact portion between the second wire 25a and the first wire 23a as shown in FIG. 11.

The second wire 25b has a recess 25br in the contact portion between the second wire 25b and the first wire 23a, and a recess 25bs in the contact portion between the second wire 25b and the first wire 23b. Further, other second wires (25c, 25d, 25e, 25f, 25g, 25h) also have recesses 25cr, recess 25cs (not shown), . . . , recess 25hr (not shown), recess 25hs. It will be easily understood.

The second wire (25a~25h) of the present embodiment has the shape of convex annular sector shape (arch shape) in the transverse plane radial direction. For example, the second wire 25a has an annular sector shape (arch shape) having a convex outer arc 25ap and a convex inner arc 25aq in the transverse plane radial direction as shown in FIG. 11.

The second wire 25b has an annular sector shape (arch shape) having a convex outer arc 25bp and a convex inner arc 25bq in the transverse plane radial direction. Further, other second wires (25c, 25d, 25e, 25f, 25g, 25h) also have annular sector shape (arch shape) having a convex outer arc and a convex inner arc in the transverse plane radial direction. It will be easily understood.

Incidentally, the tubular body 20 of the present embodiment is similar to the tubular body 10 of the second embodiment, the ends of two second wires adjacent to both sides of the first wire are separated. For example, an outer end 27a1 of the second wire 25a adjacent to one side of the first wire 23a, and an outer end 27a2 of the second wire 25b adjacent to the other side of the first wire 23a are spaced apart, further, an inner end 29a1 of the second wire 25a adjacent to one side of the first wire 23a, and an inner end 29a2 of the second wire 25b adjacent to the other side of the first wire 23a are also spaced apart as shown in FIGS. 10 and 11.

Similarly, in the other first wire 23b~23h, an outer end 27b1 and an outer end 27b2, an outer end 27c1 and an outer end 27c2, . . . , an outer end 27g1 and an outer end 27g2, an outer end 27h1 and an outer end 27h2 are spaced apart, an inner end 29b1 and an inner end 29b2, an inner end 29c1 and an inner end 29c2, . . . , an inner end 29g1 and an inner end 29g2, an inner end 29h1 and the inner end 29h2 are also spaced apart.

Accordingly, two helical patterns per one first wire are formed on the outer surface and the inner surface of the tubular body 20 as shown in FIG. 4. In the present embodiment, a total of 16 helical patterns are formed on the outer surface of the tubular body 20, and a total of 16 helical patterns are formed on the inner surface of the tubular body 20.

Similar to the first wires and a second wire of the first embodiment and the second embodiment, material of the first wires (23a~23h) and a second wire (25a~25h) are stainless steel, platinum alloys, Ni—Ti-based alloys, cobalt based alloys such as, it is not particularly limited to them. Any material having a biocompatible is available, and stainless steel is used in the present embodiment.

The first wires (23a~23h) and a second wires (25a~25h) are formed of the same material as in the present embodiment, they may be formed of a different material. However, when the tubular body 20 is produced by the method according to a swaging machine to be described above, It is preferred that the material of the second wires (25a~25h) are softer than the material of the first wires (23a~23h).

Note that the manufacturing method of the tubular body 20 is identical to the manufacturing method of the tubular body 10 of the second embodiment. However, instead of each of the second wires (15a~15h) in FIG. 7, a stranded wire configured by twisting cross-sectional view circular nine third wires is arranged.

That is, the tubular body 20 of this embodiment is produced to prepare a stranded wire configured to wind eight first wires (23a~23h) of circular cross-section and eight second wires (25a~25h) of substantially circular cross-section, wherein the diameter of the second wire is larger than the diameter of the first wire (23a~23h) in a spiral manner around the circumference of a core wire 2.

Then, after the manufacturer continues to operate the swaging machine 4 for a predetermined time in this way, while cross-sectional shape of each of eight first wires (23a~23h) is remained circular, cross-sectional shape of each of eight second wires (25a~25h) having larger diameter than the diameter of each of the first wires (23a~23h) has a recess in the contact portion between the first wire adjacent to both sides, is deformed into annular sector shape (arch shape) as shown in FIG. 10. Thereafter, similarly to the manufacturing method of the tubular body 10 of the second embodiment, by extracting the core wire 2 from the stranded wire, the tubular body 20 is completed.

According to the tubular body 20 of the present embodiment, as the tubular body 20 is configured to wind eight first wires (23a~23h) and eight second wires (25a~25h) alternately in a hollow shape, wherein each of first wires (23a~23h) is a substantially circular cross section, each of second wires (25a~25h) has a recess (25ar, 25as, 25br, 25bs, 25cr . . . 25hs) in contact portion between the first wire adjacent to it, and has an annular sector shape (arch shape) having convex outer arcs (25ap, 25bp, . . . , 25hp (not shown)) and inner arcs (25aq, 25bq, . . . 25hq (not shown)) in the transverse plane radial direction, further each of second wires (25a~25h) is configured by twisting nine third wires (such as 25a1~25a9), when the user manipulates one end portion of the tubular body 20, it is possible to prevent the deviation between the first wires and the second wires, improve the torque transmissibility and pushing force to the other end portion of the tubular body 20.

Further, since the inner surface of the tubular body 20 is flat in a vertical cross-sectional view, it may improve insertability of other medical devices into an inside of the tubular body 20. And when the user bends the tubular body 20, the subtle movement of the third wires may improve flexibility and durability of the tubular body.

In the present embodiment, the number of the first wire and the second wire is eight each, it is not limited to eight. Two or more first wires and two or more second wires may be used in a tubular body. That is, it may be a tubular body comprising a plurality of first wires and a plurality of second wires.

In the present embodiment, although the second wire is configured by twisting nine third wires, it is not limited to nine. Three or more third wires may be used in the tubular body.

Fourth Embodiment

Next, a description of a fourth embodiment of the present disclosure will be described.

FIG. 12 is a cross-sectional view of the tubular body of the fourth embodiment, FIG. 13 is a partially enlarged view of FIG. 12.

As shown in FIG. 12, a tubular body 30 is elongated tubular body configured to wind eight first wires (33a, 33b, 33c, 33d, 33e, 33f, 33g, 33h) and eight second wires (35a, 35b, 35c, 35d, 35e, 35f, 35g, 35h) alternately hollow spirally.

The tubular body 30 of the present embodiment differs from the tubular body 10 of the second embodiment, each of first wires (33a~33h) is configured to wind seven fourth wires. Specifically, the first wire 33a is configured to wind seven fourth wires (33a1, 33a2, 33a3, 33a4, 33a5, 33a6, 33a7), the first wire 3b is configured to wind seven fourth wires (33b1, 33b2, 33b3, 33b4, 333b5, 33b6, 33b7) as shown in FIG. 13.

Similarly, the other first wires 33c~33h are each configured to wind seven fourth wires (33c1~33c7, 33d1~33d7, 33e1~33e7, 33f1~33f7, 33g1~33g7, 33h1~33h7 (not one part shown)).

Further, the tubular body 30 includes a substantially circular outer peripheral surface and a substantially circular inner peripheral surface in a cross-sectional view, and the tubular body 30 forms a hollow portion 36 in an inside of the inner peripheral surface thereof.

Further, each of the second wires (35a~35h) of the present embodiment has a recess in the contact portion between the first wires adjacent to both sides. For example, the second wire 35a has a recess 35ar in the contact portion between the second wire 35a and the first wire 33h, and a recess 35as in the contact portion between the second wire 35a and the first wire 33a as shown in FIG. 13.

The second wire 35b has a recess 35br in the contact portion between the second wire 35b and the first wire 33a, and a recess 35bs in the contact portion between the second wire 35b and the first wire 33b. Further, other second wires (35c, 35d, 35e, 35f, 35g, 35h) also have recesses 35cr, recess 35cs (not shown), . . . , recess 35hr (not shown), recess 35hs. It will be easily understood.

The second wire (35a~35h) of the present embodiment has the shape of convex annular sector shape (arch shape) in the transverse plane radial direction. For example, the second wire 35a has an annular sector shape (arch shape) having a convex outer arc 35ap and a convex inner arc 35aq in the transverse plane radial direction as shown in FIG. 13.

The second wire 35b has an annular sector shape (arch shape) having a convex outer arc 35bp and a convex inner arc 35bq in the transverse plane radial direction. Further, other second wires (35c, 35d, 35e, 35f, 35g, 35h) also have annular sector shape (arch shape) having a convex outer arc and a convex inner arc in the transverse plane radial direction. It will be easily understood.

Incidentally, the tubular body 30 of the present embodiment is similar to the tubular body 10 of the second embodiment, the ends of two second wires adjacent to both sides of the first wire are separated. For example, an outer end 37a1 of the second wire 35a adjacent to one side of the first wire 33a, and an outer end 37a2 of the second wire 35b adjacent to the other side of the first wire 33a are spaced apart, further, an inner end 39a1 of the second wire 35a adjacent to one side of the first wire 33a, and an inner end 39a2 of the second wire 35b adjacent to the other side of the first wire 33a are also spaced apart as shown in FIGS. 12 and 13.

Similarly, in the other first wire 33b~33h, an outer end 37b1 and an outer end 37b2, an outer end 37c1 and an outer end 37c2, . . . , an outer end 37g1 and an outer end 37g2, an outer end 37h1 and an outer end 37h2 are spaced apart, an inner end 39b1 and an inner end 39b2, an inner end 39c1 and an inner end 39c2, . . . , an inner end 39g1 and an inner end 39g2, an inner end 39h1 and the inner end 39h2 are also spaced apart.

Accordingly, two helical patterns per one first wire are formed on the outer surface and the inner surface of the tubular body 30 as shown in FIG. 4. In the present embodiment, a total of 16 helical patterns are formed on the outer surface of the tubular body 30, and a total of 16 helical patterns are formed on the inner surface of the tubular body 30.

Similar to the first wires and a second wire of the first embodiment to the third embodiment, material of the first wires (33a~33h) and a second wire (35a~35h) are stainless steel, platinum alloys, Ni—Ti-based alloys, cobalt based alloys such as, it is not particularly limited to them. Any material having a biocompatible is available, and stainless steel is used in the present embodiment.

The first wires (33a~33h) and a second wires (35a~35h) are formed of the same material as in the present embodiment, they may be formed of a different material. However, when the tubular body 30 is produced by the method according to a swaging machine to be described before, It is preferred that the material of the second wires (35a~35h) are softer than the material of the first wires (33a~33h).

Note that the manufacturing method of the tubular body 30 is identical to the manufacturing method of the tubular body 10 of the second embodiment. However, instead of each of the first wires (13a~13h) in FIG. 7, a stranded wire configured by twisting cross-sectional view circular seven fourth wires is arranged.

That is, the tubular body 30 of this embodiment is produced to prepare a stranded wire configured to wind eight first stranded wires (33a~33h) configured to wind seven fourth wires of circular cross-section and eight second wires (35a~35h) of circular cross-section, wherein the diameter of the second wire is larger than the diameter of the first wire (33a~33h), in a spiral manner around the circumference of a core wire 2.

Then, after the manufacturer continues to operate the swaging machine 4 for a predetermined time in this way, while cross-sectional shape of each of eight first wires (33a~33h) is remained circular, cross-sectional shape of each of eight second wires (35a~35h) having larger diameter than the diameter of each of the first wires (33a~33h) has a recess in the contact portion between the first wire adjacent to both sides, is deformed into annular sector shape (arch shape) as shown in FIG. 12. Thereafter, similarly to the manufacturing method of the tubular body 10 of the second embodiment, by extracting the core wire 2 from the stranded wire, the tubular body 30 is completed.

According to the tubular body 30 of the present embodiment, as the tubular body 30 is configured to wind eight first wires (33a~33h) and eight second wires (35a~35h) alternately in a hollow shape, wherein each of first wires (33a~33h) is a substantially circular cross section, each of second wires (35a~35h) has recesses (35ar, 35as, 35br, 35bs, 35cr . . . 35hs) in contact portion between the first wire adjacent to it, and has an annular sector shape (arch shape) having convex outer arcs (35ap, 35bp, . . . , 35hp (not shown)) and inner arcs (35aq, 35bq, . . . 35hq (not shown)) in the transverse plane radial direction, further each of first wires (33a~33h) is configured by twisting seven fourth wires (such as 33a1~33a7), when the user manipulates one end portion of the tubular body 30, it is possible to prevent the deviation between the first wires and the second wires, improve the torque transmissibility and pushing force to the other end portion of the tubular body 30.

Further, since the inner surface of the tubular body 30 is flat in a vertical cross-sectional view, it may improve insertability of other medical devices into an inside of the tubular body 30. And when the user bends the tubular body 30, the subtle movement of the fourth wires may improve flexibility and durability of the tubular body.

In the present embodiment, the number of the first wire and the second wire is eight each, it is not limited to eight. Two or more first wires and two or more second wires may be used in a tubular body. That is, it may be a tubular body comprising a plurality of first wires and a plurality of second wires.

In the present embodiment, although the first wire is configured by twisting seven fourth wires, it is not limited to seven. Three or more fourth wires may be used in the tubular body.

Fifth Embodiment

Next, a description of a fifth embodiment of the present disclosure will be described.

FIG. 14 is a cross-sectional view of the tubular body of the fifth embodiment, FIG. 15 is a partially enlarged view of FIG. 14.

As shown in FIG. 14, a tubular body 40 is elongated tubular body configured to wind eight first wires (43a, 43b, 43c, 43d, 43e, 43f, 43g, 43h) and eight second wires (45a, 45b, 45c, 45d, 45e, 45f, 45g, 45h) alternately hollow spirally.

The tubular body 40 of the present embodiment differs from the tubular body 10 of the second embodiment, each of first wires (43a~43h) is configured to wind seven fourth wires, each of second wires (45a~45h) is configured to wind nine third wires.

Specifically, the first wire 43a is configured to wind seven fourth wires (43a1, 43a2, 43a3, 43a4, 43a5, 43a6, 43a7), the second wire 45a is configured to wind nine third wires (45a1, 45a2, 45a3, 45a4, 45a5, 45a6, 45a7, 45a8, 45a9) as shown in FIG. 15.

Similarly, the other first wires 43b~43h are each configured to wind seven fourth wires (43b1~43b7, 43c1~43c7, 43d1~43d7, 43e1~43e7, 43f1~43f7, 43g1~43g7, 43h1~43h7 (not one part shown)), the other second wires 45b~45h are each configured to wind nine third wires (45b1~45b9, 45c1~45c9, 45d1~45d9, 45e1~45e9, 45f1~45f9, 45g1~45g9, 45h1~45h9 (not one part shown)).

Further, the tubular body 40 includes a substantially circular outer peripheral surface and a substantially circular inner peripheral surface in a cross-sectional view, and the tubular body 40 forms a hollow portion 46 in an inside of the inner peripheral surface thereof.

Further, each of the second wires (45a~45h) of the present embodiment has a recess in the contact portion between the first wires adjacent to both sides. For example, the second wire 45a has a recess 45ar in the contact portion between the second wire 45a and the first wire 43h, and a recess 45as in the contact portion between the second wire 45a and the first wire 43a as shown in FIG. 15.

The second wire 45b has a recess 45br in the contact portion between the second wire 45b and the first wire 43a, and a recess 45bs in the contact portion between the second wire 45b and the first wire 43b. Further, other second wires (45c, 45d, 45e, 45f, 45g, 45h) also have recesses 45cr, . . . , recess 45hs. It will be easily understood.

The second wire (45a~45h) of the present embodiment has the shape of convex annular sector shape (arch shape) in the transverse plane radial direction. For example, the second wire 45a has an annular sector shape (arch shape) having a convex outer arc 45ap and a convex inner arc 45aq in the transverse plane radial direction as shown in FIG. 15.

The second wire 45b has an annular sector shape (arch shape) having a convex outer arc 45bp and a convex inner arc 45bq in the transverse plane radial direction. Further, other second wires (45c, 45d, 45e, 45f, 45g, 45h) also have annular sector shape (arch shape) having a convex outer arc and a convex inner arc in the transverse plane radial direction. It will be easily understood.

Incidentally, the tubular body 40 of the present embodiment is similar to the tubular body 10 of the second embodiment, the ends of two second wires adjacent to both sides of the first wire are separated. For example, an outer end 47a1 of the second wire 45a adjacent to one side of the first wire 43a, and an outer end 47a2 of the second wire 45b adjacent to the other side of the first wire 43a are spaced apart, further, an inner end 49a1 of the second wire 45a adjacent to one side of the first wire 43a, and an inner end 49a2 of the second wire 45b adjacent to the other side of the first wire 43a are also spaced apart as shown in FIGS. 14 and 15.

Similarly, in the other first wire 43b~43h, an outer end 47b1 and an outer end 47b2, an outer end 47c1 and an outer end 47c2, . . . , an outer end 47g1 and an outer end 47g2, an outer end 47h1 and an outer end 47h2 are spaced apart, inner end 49b1 and an inner end 49b2, an inner end 49c1 and an inner end 49c2, . . . , an inner end 49g1 and an inner end 49g2, an inner end 49h1 and the inner end 49h2 are also spaced apart.

Accordingly, two helical patterns per one first wire are formed on the outer surface and the inner surface of the tubular body 40 as shown in FIG. 4. In the present embodiment, a total of 16 helical patterns are formed on the outer surface of the tubular body 40, and a total of 16 helical patterns are formed on the inner surface of the tubular body 40.

Similar to the first wires and a second wire of the first embodiment to the fourth embodiment, material of the first wires (43a~43h) and a second wire (45a~45h) are stainless steel, platinum alloys, Ni—Ti-based alloys, cobalt based alloys such as, it is not particularly limited to them. Any material having a biocompatible is available, and stainless steel is used in the present embodiment.

The first wires (43a~43h) and a second wires (45a~45h) are formed of the same material as in the present embodiment, they may be formed of a different material. However, when the tubular body 40 is produced by the method according to a swaging machine to be described before, It is preferred that the material of the second wires (45a~45h) are softer than the material of the first wires (43a~43h).

Note that the manufacturing method of the tubular body 40 is identical to the manufacturing method of the tubular body 10 of the second embodiment. However, instead of each of the first wires (13a~13h) in FIG. 7, a stranded wire configured by twisting seven cross-sectional view circular fourth wires is arranged. And instead of each of the second wires (15a~15h) in FIG. 7, a stranded wire configured by twisting nine cross-sectional view circular third wires is arranged.

That is, the tubular body 40 of this embodiment is produced to prepare a stranded wire configured to wind eight first stranded wires (43a~43h) configured to wind seven fourth wires of circular cross-section and eight second wires (45a~45h) of circular cross-section, wherein the diameter of the second wire is larger than the diameter of the first wire (43a~43h), in a spiral manner around the circumference of a core wire 2.

Then, after the manufacturer continues to operate the swaging machine 4 for a predetermined time in this way, while cross-sectional shape of each of eight first wires (43a~43h) is remained circular, cross-sectional shape of each of eight second wires (45a~45h) having larger diameter than the diameter of each of the first wires (43a~43h) has a recess in the contact portion between the first wire adjacent to both sides, is deformed into annular sector shape (arch shape) as shown in FIG. 14. Thereafter, similarly to the manufacturing method of the tubular body 10 of the second embodiment, by extracting the core wire 2 from the stranded wire, the tubular body 40 is completed.

According to the tubular body 40 of the present embodiment, as the tubular body 40 is configured to wind eight first wires (43a~43h) and eight second wires (45a~45h) alternately in a hollow shape, wherein each of first wires (433a~43h) is a substantially circular cross section, each of second wires (45a~45h) has a recess (45ar, 45as, 45br, 45bs, 45cr . . . 45hs) in contact portion between the first wire adjacent to it, and has an annular sector shape (arch shape) having convex outer arcs (45ap, 45bp, . . . , 45hp (not shown)) and inner arcs (45aq, 45bq, . . . 45hq (not shown)) in the transverse plane radial direction, further each of first wires (43a~43h) is configured by twisting seven fourth wires (such as 43a1~43a7), when the user manipulates one end portion of the tubular body 40, it is possible to prevent the deviation between the first wires and the second wires, improve the torque transmissibility and pushing force to the other end portion of the tubular body 40.

Further, since the inner surface of the tubular body 40 is flat in a vertical cross-sectional view, it may improve insertability of other medical devices into an inside of the tubular body 40. And when the user bends the tubular body 40, the subtle movement of the third wires and the subtle movement of the fourth wires may improve flexibility and durability of the tubular body.

In the present embodiment, the number of the first wire and the second wire is eight each, it is not limited to eight. Two or more first wires and two or more second wires may be used in a tubular body. That is, it may be a tubular body comprising a plurality of first wires and a plurality of second wires.

In the present embodiment, although the first wire is configured by twisting seven fourth wires, it is not limited to seven. Three or more fourth wires may be used in the tubular body.

In the present embodiment, although the second wire is configured by twisting nine third wires, it is not limited to nine. Three or more third wires may be used in the tubular body.

DESCRIPTION OF THE CODE 1, 10, 20, 30, 40 . . . tubular body
2 . . . core wire
3a~3h, 13a~13h, 23a~23h, 33a~33h, 43a~43h . . . first wire
4 . . . swaging machine
5a~5h, 15a~15h, 25a~25h, 35a~35h, 45a~45h . . . second wires
6, 16, 26, 36, 46 . . . hollow portion
7a~7h, 17a~17h, 27a~27h, 37a~37h, 47a~47h . . . outer end
9a~9h, 19a~19h, 29a~29h, 39a~39h, 49a~49h . . . inner end

The invention claimed is:

1. A tubular body, comprising:
a plurality of first wires distributed in an annular portion of the tubular body; and
a plurality of deformed second wires alternately disposed between each of the plurality of first wires, the plurality of first wires and the plurality of deformed second wires being in an alternately twisted arrangement in a longitudinal direction of the tubular body, wherein
each of the plurality of first wires has a substantially circular shape in a cross section view with respect to the longitudinal direction of the tubular body,
each of the plurality of deformed second wires has a non-circular shape in the cross section view, has an arcuate side portion that receive a part of a side surface of an adjacent wire of the plurality of first wires, has an annular sector shape protruding in a radial direction in the cross section view of the tubular body, and is configured by twisting a plurality of third wires to form the non-circular shape having the arcuate side portion and the annular sector shape, and
each of the plurality of third wires has an arch shape protruding in a radial direction in the cross section view of the tubular body.

2. The tubular body according to claim 1,
wherein each of the plurality of first wires is configured by twisting a plurality of fourth wires.

3. The tubular body according to claim 2,
wherein the number of the plurality of fourth wires is three or more.

4. The tubular body according to claim 3,
wherein the number of the plurality of fourth wires is seven.

5. The tubular body according to claim 1,
wherein each of the plurality of deformed second wires is formed by deforming a second wire having a larger diameter than a diameter of the first wire.

6. The tubular body according to claim 1,
wherein the tubular body has a substantially circular shape in the cross section view.

7. The tubular body according to claim 1,
wherein the number of the plurality of first wires is eight and the number of the plurality of deformed second wires is eight.

8. The tubular body according to claim 1,
wherein the number of the plurality of third wires is three or more.

9. The tubular body according to claim 8,
wherein the number of the plurality of third wires is nine.

10. The tubular body according to claim 1,
wherein any one of ends of the plurality of the third wires constituting two deformed second wires adjacent to both sides of the first wire is in contact with each other at one point on an outer surface of the tubular body and at another point on an inner surface of the tubular body.

11. The tubular body according to claim 1,
wherein any one of ends of the plurality of the third wires constituting two deformed second wires adjacent to both sides of the first wire is in contact with each other at least at a first point on an outer surface of the tubular body and at a second point on an inner surface of the tubular body.

12. The tubular body according to claim 1, wherein any end of the plurality of the third wires constituting two deformed second wires adjacent to both sides of the first wire is not in contact with each other.

13. The tubular body according to claim 1, wherein the plurality of first wires and the plurality of deformed second wires are made of biocompatible materials.

14. The tubular body according to claim 1, wherein the plurality of first wires are made of at least one of stainless steel, platinum alloys, Ni—Ti-based alloys, and cobalt based alloys, and
the plurality of deformed second wires are made of at least one of stainless steel, platinum alloys, Ni—Ti-based alloys, and cobalt based alloys.

15. The tubular body according to claim 1, wherein a second material of the plurality of deformed second wires is softer than a first material of the plurality of first wires.

16. The tubular body according to claim 1, wherein each of the plurality of the third wires is made of metal and is in contact with adjacent third wires each other.

* * * * *